(12) United States Patent
Frerot et al.

(10) Patent No.: US 6,939,835 B2
(45) Date of Patent: Sep. 6, 2005

(54) CYCLIC COMPOUNDS AND THEIR USE AS PRECURSORS OF FRAGRANT ALCOHOLS

(75) Inventors: Eric Frerot, Ville-la-Grand (FR); Jean-Yves Billard de Saint-Laumer, Beaumont (FR); Otto Gräther, Carouge (CH)

(73) Assignee: Firmenich SA, Geneva (CH)

( * ) Notice: Subject to any disclaimer, the term of this patent is extended or adjusted under 35 U.S.C. 154(b) by 185 days.

(21) Appl. No.: 10/353,919

(22) Filed: Jan. 30, 2003

(65) Prior Publication Data

US 2003/0148901 A1 Aug. 7, 2003

Related U.S. Application Data

(63) Continuation-in-part of application No. 09/943,192, filed on Aug. 30, 2001, now abandoned, which is a continuation of application No. PCT/IB00/00315, filed on Mar. 21, 2000.

(30) Foreign Application Priority Data

Mar. 26, 1999 (CH) ............................................... 0579/99

(51) Int. Cl.$^7$ ............................ C11D 3/50; A61K 7/46; C07C 69/76
(52) U.S. Cl. ......................... 510/102; 512/21; 560/105
(58) Field of Search .......................... 510/102; 512/21; 560/105

(56) References Cited

U.S. PATENT DOCUMENTS

| 4,624,802 A | 11/1986 | Schaper .................. 252/522 R |
| 4,695,648 A | 9/1987 | Agback et al. ................ 560/53 |
| 5,214,204 A | 5/1993 | Dellaria et al. ............. 562/623 |
| 5,562,847 A | * 10/1996 | Waite et al. ................ 510/519 |
| 5,652,206 A | * 7/1997 | Bacon et al. ............... 510/101 |
| 5,721,202 A | * 2/1998 | Waite et al. ................ 510/102 |
| 6,024,943 A | * 2/2000 | Ness et al. ..................... 424/59 |

FOREIGN PATENT DOCUMENTS

| DE | 197 50 706 A1 | 5/1998 |
| GB | 2 319 527 | 5/1998 |
| JP | 61197552 | 9/1996 |
| WO | WO 95/04809 | 2/1995 |
| WO | WO 98/07814 | 2/1998 |
| WO | WO 98/47478 | 10/1998 |

OTHER PUBLICATIONS

O. V. Topalova, Deposited Document 1975, VINITI 2990–75, pages. No month available.*
C. D. Gutsche et al., Journal of the American Chemical Society, vol. 90, pp. 5855–5861, Oct. 1968.*
Beilstein Information Service File: XFire, XP002140854. see BRBs: 4504558, 4251994, 2693192, 2651922, 4812476, 3106865, 4747981, Jul. 1992.

L Horner et al., "Moglichkeiten und Grenzen phototochemisch induzierter asymmetrischer Synthesen", Verlag Chemie, GmbH pp. 1232–1257 (1979), no month available.
A. Kotali et al, "Synthesis Of o–Ketoaryl–Carboxylic Esters Using Phenyliodoso Diacetate",OPPI Briefs, vol. 28, No. 5 pp. 622–627 (1996), no month available.
H. Gordon et al, "Optical Activity and the Polarity of Substituent Groups. Part III. Menthyl Acetophenone–o–carboxylate", Journal of Chem. Science, pp. 553–556 (1926), no month available.
M. Vivekananda Bhatt et al., "Aspects of Tautomerism, 6$^{1a,b}$ Base–Catalyzed Hydrolysis of Pseudo Esters ofγ–keto Acids", J. Org. Chem., vol. 42, No. 16, pp. 2697–2701 (1977), no month available.
N. Gautier et al., "The Practical Use of a Glycine Anion Equivalent For The Preparation of 3–Carboxy–1–2–Dihydro–1–Oxoisoquinoline" Synthetic Communications, vol. 28, No. 20, pp. 3769–3977 (1998), no month available.
Bram et al, "Solid–Liquid Phase Transfer Catlysis without Addied Solvern. A Simple, Efficient, and Inexpensive Synthesis of Aromatic Carboxylic Esters By Alkylation of Patasium Carboxylates" Communications, pp. 40–45 (1985), no month available.

* cited by examiner

Primary Examiner—John R. Hardee
(74) Attorney, Agent, or Firm—Winston & Strawn LLP

(57) ABSTRACT

Compounds of the formula

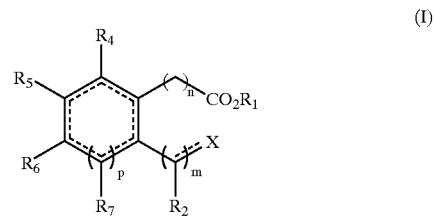

(I)

in which the dotted lines indicate the position of single or double bonds, $R_1$ represents a radical belonging to a fragrant alcohol of the formula $R_1OH$, X represents a nucleophilic group selected from the group consisting of —OH, =O, —NH$_2$ or —NHR$_3$, $R_3$ representing a $C_1$ to $C_6$ straight-chain or branched hydrocarbon radical, saturated or unsaturated, or an aliphatic or aromatic ring having 5 or 6 carbon atoms, m and n define whole numbers within the range 0 to 2 such that the sum m+n is equal to 1 or 2, p defines a whole number with a value of 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted and, taken two by two, they can form aromatic or aliphatic monocyclic, bicyclic or tricyclic substances with the carbon atoms to which they are bound, are compounds capable of releasing a fragrant alcohol of the formula $R_1OH$ upon hydrolysis of the ester bond.

15 Claims, No Drawings

CYCLIC COMPOUNDS AND THEIR USE AS PRECURSORS OF FRAGRANT ALCOHOLS

CROSS-REFERENCE TO RELATED APPLICATIONS

This application is a continuation-in-part of application Ser. No. 09/943,192 filed Aug. 30, 2001 now abandoned, which in turn is a continuation of International application PCT/IB00/00315 filed Mar. 21, 2000.

TECHNICAL FIELD

The present invention relates to the perfume industry. More particularly, it is concerned with new cyclic compounds capable of releasing fragrant alcohols.

BACKGROUND

The perfume industry is displaying a particular interest in compounds which are able to prolong a fragrancing effect for a period of time, in particular to mitigate the problems encountered when using volatile perfuming ingredients. Compounds are known which, only under certain conditions of activation such as light, heat, or the presence of enzymes, notably lipases, are capable of releasing a fragrant substance over an extended time period. For example, international patent application WO 95/04809, which belongs to the present applicant, discloses a process for perfuming fabrics washed in the presence of a lipase-containing detergent comprising a compound of formula

The lipase constitutes an activating agent which is necessary to provide the release of a perfuming molecule from the cited compound. These compounds may be used in various applications. The washing of textiles in particular is a field in which scientists are always searching for new means enabling the effect of perfuming substances to be perceived for a period of time after the washing and drying operations. This because many substances which have odours especially suitable for this type of application are known not to be long-lasting on washed items, with the result that their perfuming effect is perceived only briefly. Given the importance of this type of application in the perfume industry, research activity is on-going within this sector, notably with the aim of finding ever more effective solutions to solve the problems mentioned above.

SUMMARY OF THE INVENTION

We have now surprisingly discovered the existence of new cyclic compounds that are capable of releasing fragrant alcohols over a long period of time under totally unforeseen and advantageous conditions, that is to say, without any external assistance or activation condition. Thus, contrary to what is known in the prior art, the process of release of a fragrant alcohol by the compounds of the invention does not necessitate the presence of an external catalyst in the reaction medium, for example an enzyme and in particular a lipase. In an application when they are incorporated in a perfume formulation or in a functional article that has to be perfumed such as a detergent and/or a fabric softener of any kind, these compounds thus enable the characteristic odour of the alcohol to be imparted to a surface such as a textile and also enable the diffusion effect of this odour to be prolonged so that it develops over a period of time.

The compounds of the invention comply with the following formula,

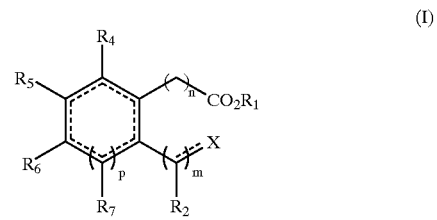

in which the dotted lines indicate the position of single or double bonds, $R_1$ represents a radical belonging to a fragrant alcohol of the formula $R_1OH$ comprising at least four carbon atoms, X represents a nucleophilic group selected from the group consisting of —OH, =O, —NH$_2$ or —NHR$_3$, $R_3$ representing a $C_1$ to $C_6$ straight-chain or branched hydrocarbon radical, saturated or unsaturated, or an aliphatic or aromatic ring having 5 or 6 carbon atoms, m and n define whole numbers within the range 0 to 2 such that the sum m+n is equal to 1 or 2, p defines a whole number with a value of 0 or 1, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted and, taken two by two, they can form aromatic or aliphatic monocyclic, bicyclic or tricyclic substances with the carbon atoms to which they are bound.

DETAILED DESCRIPTION OF THE PREFERRED EMBODIMENTS

Of the compounds of formula (I), menthyl-2-acetylbenzoate has been described by H. G. Rule and J. Smith in J. Chem. Soc., 1926, 553 and by L. Homer and J. Klaus in Liebigs Ann. Chem., 1979, 1232. Similarly, menthyl 2-formylbenzoate has been described by M. V. Bhatt et al. in J. Org. Chem., 1977, 42, 2697, benzyl 2-formylbenzoate has been described by N. Gautier and R. H. Dodd in Synth. Commun., 1998, 28, 3769, octyl 2-formylbenzoate by J. Barry et al., Synthesis, 1985, 40, and finally benzyl 2-acetylbenzoate by A. Kotali et al., Org. Prep. Proced. Int., 1996, 28, 622. However, these documents of the prior art contain no mention, description or suggestion of any use of these compounds in perfumery for any purposes. In particular, there is no disclosure of the use of these compounds as precursors susceptible of releasing fragrant alcohols.

The compounds of the invention are capable of releasing a fragrant alcohol of the formula $R_1OH$ on hydrolysis of their ester bond. Fragrant alcohol here means an alcohol comprising at least four carbon atoms, currently used in the formulation of perfumes or perfumed articles, that is to say, one which is useable as a perfuming ingredient for the preparation of perfumes or perfumed articles, i.e. an ingredient capable of imparting, enhancing or modifying the odor properties of a composition or product to which it is added. The criteria to be met as a useable perfuming ingredient are known to the person skilled in the art and include, notably, a certain originality of the fragrance, stability, or even a favourable cost/effectiveness ratio. Although it is obviously impossible to provide an exhaustive list of known alcohols comprising at least four carbon atoms of the formula $R_1OH$ which may be used according to the invention, we mention by way of example anisyl alcohol, fenchyl alcohol, cinnamic alcohol, 9-decen-1-ol, phenethylol, citronellol (3,7-dimethyl-6-octen-1-ol), 3-methyl-5-phenyl-1-pentanol (source: Firmenich S. A., Geneva, Switzerland), Mayol® (7p-menthan-1-ol; source: Firmenich S. A., Geneva, Switzerland), dihydromyrcenol (2,6-dimethyl-oct-7-ene-2-ol), alpha-ionol, tetrahydro-ionol, geraniol [(E)-3,7-dimethyl-2,6-octadien-1-ol], nerol (Z)-3,7-dimethyl-2-6-octadien-1-ol, (Z)-3-hexen-1-ol, 1-hexanol, 2-hexanol, 3,3,5-trimethylhexanol, 3,4,5,6,6-pentamethyl-heptan-2-ol, 5-ethyl-2-nonanol, (Z)-6-nonenol, 6,8-dimethyl-2-nonanol, 2,6-nonadien-1-ol, borneol, 1-octen-3-ol, 4-cyclohexyl-2-methyl-2-butanol (source: Firmenich S. A., Geneva, Switzerland), 6-ethyl-3-methyl-5-octen-1-ol, 3,7-dimethyl-oct-3,6-dienol, 7-methoxy-3,7-dimethyl-octan-2-ol, methyl-4-phenyl-2-butanol, 2-methyl-1-phenyl-2-propanol, 1-phenylethanol, 2-phenylethanol, 2-phenylpropanol, 3-phenylpropanol, 2-methyl-5-phenylpentanol, 2-methyl-4-phenylpentanol, 3-methyl-5-phenylpentanol, cyclomethyl-citronellol, decanol, dihydroeugenol, 8-p-methanol, 3,7-dimethyl-1-octanol, 2,6-dimethyl-2-heptanol, dodecanol, octanol, undecanol, 4-methyl-3-decen-1-ol, eugenol, Florol® (tetrahydro-2-isobutyl-4-methyl-4(2H)-pyranol; source: Firmenich S. A., Geneva, Switzerland), 2-phenoxy-ethanol, isoeugenol, linalol, Tarragol® (2-methoxy-4-propyl-1-cyclohexanol; source: Firmenich S. A., Geneva, Switzerland), vanillin, ethyl-vanillin, anethol, farnesol, cedrenol, menthol, p-menth-8-en-3-ol, 3,3,5-trimethyl-cyclohexanol, 2,4,6-trimethyl-3-cyclohexenyl-methanol, 4-(1-methylethyl)cyclohexyl-methanol, terpineol, tetrahydromugol, 3,7-dimethyl-3-octanol, Polysantol® [(E)-3,3-dimethyl-5-(2',2',3'-trimethyl-3'-cyclopenten-1-yl)-4-penten-2-ol; source: Firmenich S. A., Geneva, Switzerland), 2,2,6-trimethyl-alpha-propyl-cyclohexane propanol, 5-(2,2,3-trimethyl-3-cyclopentyl)-3-methylpentan-2-ol, 3-methyl-5-(2,2,3-trimethylcyclopent-3-enyl)pent-4-en-2-ol, 2-ethyl-4-(2,2,3-trimethylcyclopent-3-enyl)but-2-en-1-ol, 4-(5,5,6-trimethylbicyclo[2.2.1]hept-2-yl)-cyclohexanol, 2-(2-methyl-propyl)-4-hydroxy-4-methyl-tetrahydropyrane, 2-cyclohexyl propanol, 2-(1,1-dimethyl-ethyl)-4-methyl-cyclohexanol, 1-(2-tert-butyl-cyclo hexyloxy)-2-butanol, 1-(4-isopropyl-cyclohexyl)-ethanol, Limbanol® [1-(2,2,3,6-tetramethyl-cyclohex-1-yl)-3-hexanol; source: Firmenich S. A., Geneva, Switzerland), 1-heptanol, 1-nonanol and 10-undecen-1-ol. It goes without saying that this list is not complete, any alcohol capable of imparting an odor to a product to be perfumed being comprised in the alcohols comprising at least four carbon atoms of formula $R_1OH$ related to the invention.

The characteristic feature of the invention resides in the fact that the hydrolysis which induces the release of alcohol is facilitated by an auxiliary effect of the ester bond's neighbouring nucleophilic group X. This effect provides a totally unexpected advantage, that is, it permits cleavage of the ester bond by hydrolysis under simple alkaline conditions, as shown diagrammatically below:

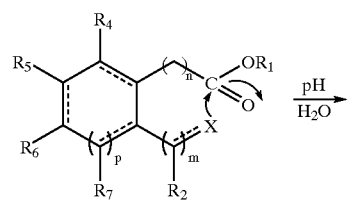

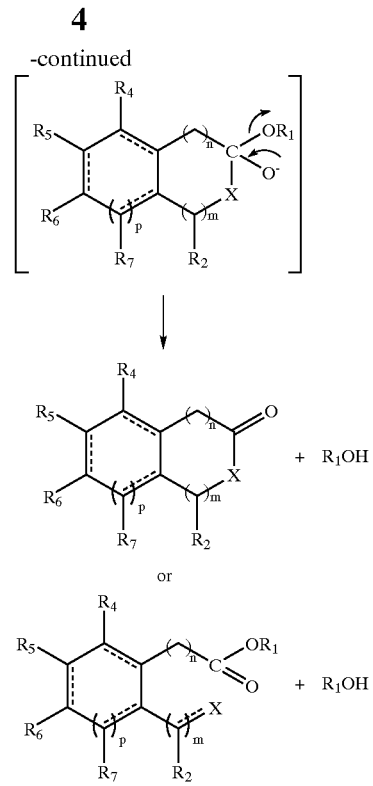

Examples are the conventional conditions of textiles washing, in the course of which a change in pH occurs. The pH passes from a value corresponding to an acid medium to values corresponding to a neutral or even a basic medium during the washing cycle, thus enabling the compounds of the invention to be hydrolysed.

Otherwise the reaction is catalysed naturally in the presence of heat. This occurs for example when washing is dried, namely in a tumble-dryer. The hydrolysis reaction leads to the formation of an odoriferous substance $R_1OH$ wherein $R_1$ has the meaning indicated above, and of a residue of the initial precursor, which is generally odourless.

The reaction requires no activation condition such as the presence of a lipase in the detergent, as reported in the prior art (WO 95/04809).

We also noticed that the preferred compounds according to the invention exhibit a common characteristic enabling them to benefit from this auxiliary effect of the neighbouring group for hydrolysis of the ester bond. The compounds claimed are in fact capable of assuming a constrained conformation in which the distance between the oxygen or nitrogen of the nucleophilic group X and the carbon of the ester function does not exceed 2.8 Angström for a molecular energy calculated by the method MM2 (molecular mechanical) which differs by no more than 3 kcal/mol from the minimum total energy of the molecule.

"Constrained conformation" is here understood to mean a conformation different from the most stable conformation of the molecule and the achievement of which requires a specific quantity of energy relative to the minimum energy of the molecule, that is, the energy of the molecule in its most stable conformation. The respective molecular energy values are molecular parameters established for each compound with the aid of a model SGI R10000 computer using a MacroModel V6.5 programme (F. Mohamadi et al., J. Comput. Chem. 1990, 11, 440). The minimum total energies are obtained by the method known from the prior art, designated by method MM2 and by the Monte Carlo procedure executed on MacroModel. The energies of the constrained conformations are defined in accordance with the same method. We were surprised to discover that the compounds exhibiting the above-mentioned distance and energy constraints were capable of prolonged release of the fragrant alcohol $R_1OH$ over time and under the normal conditions of application, i.e. for instance, when these compounds are used in the treatment of textiles or various other surfaces.

Amongst the compounds of the invention according to formula (I) in which X represents an =O group, the 2-acyl-benzoates of the formula

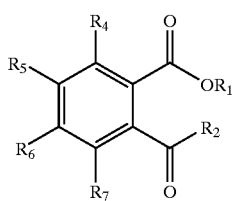

(Ia)

are appreciated.

Preferentially one may cite 3,7-dimethyl-6-octenyl 2-formylbenzoate, (E or Z)-3,7-dimethyl-2,6-octadienyl 2-formylbenzoate, 2-phenylethyl 2-formylbenzoate, (E)-3,7-dimethyl-2,6-octadienyl 2-acetylbenzoate, 3,7-dimethyl-6-octenyl 2-acetylbenzoate, and (1R, 3R, 4S)-3-p-menthanyl 2-acetylbenzoate. Of the preferred compounds defined above, the ones most preferred are 3,7-dimethyl-6-octenyl 2-formylbenzoate, (E)-3,7-dimethyl-2,6-octadienyl 2-formylbenzoate, phenylethyl 2-formylbenzoate and (E)-3,7-dimethyl-2,6-octadienyl 2-acetylbenzoate.

On the other hand, the preferred compounds among those of the invention of formula (I) in which X defines an —OH group are the 2-hydroxymethylbenzoates and the esters of dihydrocoumaric acid, of the respective formulae

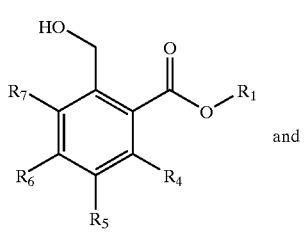

(Ib)

and (Ic)

One may cite in particular a preference for 3-p-menthanyl 2-hydroxy-methylbenzoate, 3,7-dimethyl-6-octenyl 2-hydroxymethylbenzoate, 2-phenyl-ethyl 2-hydroxymethylbenzoate, (Z)-3-hexenyl 2-hydroxymethylbenzoate, (E)-3,7-dimethyl-2,6-octadienyl 2-hydroxymethylbenzoate, 1-p-menthen-8-yl 2-hydroxymethylbenzoate, (1'R,E)-1,2,2-trimethyl-4-(2',2',3'-trimethyl-3'-cyclopenten-1'-yl)-3-butenyl 2-hydroxymethylbenzoate, (Z)-3-hexenyl dihydrocoumarate, (E)-3,7-dimethyl-2,6-octa-dienyl dihydrocoumarate and (Z)-3-hexenyl 3-endo-hydroxymethyl-bicyclo[2.2.1]hept-5-ene-2-endo-carboxylate.

The compounds of the invention may be prepared starting from commercially available compounds and with the aid of conventional methods. Thus in a general way, starting with commercially available starting materials (acids or anhydrides) an ester bond is produced by conventional esterification of carboxyls, or by acid catalysis. Then, if necessary, the residual function (acid, aldehyde or ketone) corresponding to the future nucleophilic function is functionalized by reduction or reductive amination depending on the precursor required.

For example, the 2-acyl- and 2-formyl-benzoates are prepared on the basis of corresponding acids by simple esterification according to the following scheme:

Scheme 1

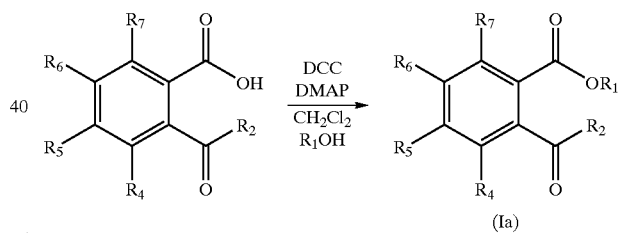

(Ia)

DCC: dicyclohexylcarbodiimide
DMAP: 4-dimethylaminopyridine

Other compounds such as the 2-hydroxymethylbenzoates may be prepared from the corresponding phthalates, as shown in the scheme below:

Scheme 2

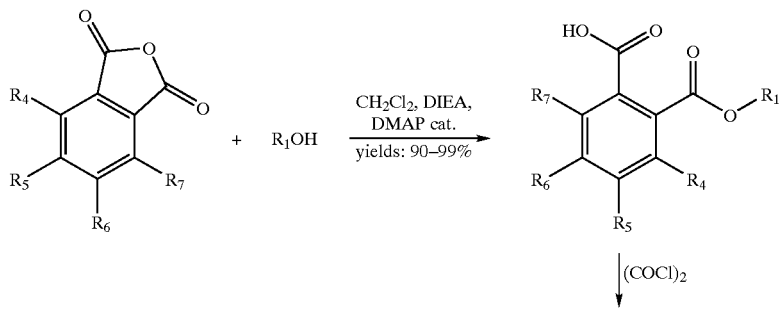

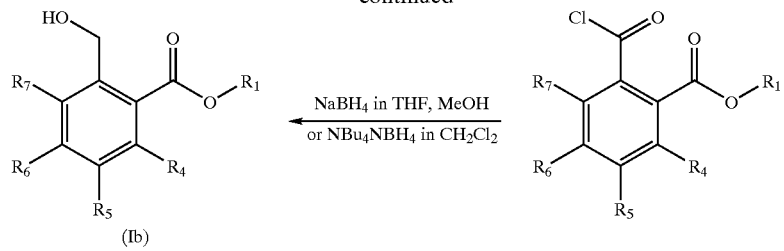

DIEA: diisopropylethylamine
DMAP: 4-dimethylaminopyridine
(COCl$_2$): oxalyl chloride
NaBH$_4$: sodium boron hydride
THF: tetrahydrofuran
Bu$_4$NBH$_4$: tetrabutylammonium boron hydride According to another example, esters of dihydrocoumaric acid may be prepared from o-coumaric acid as follows:

Scheme 3

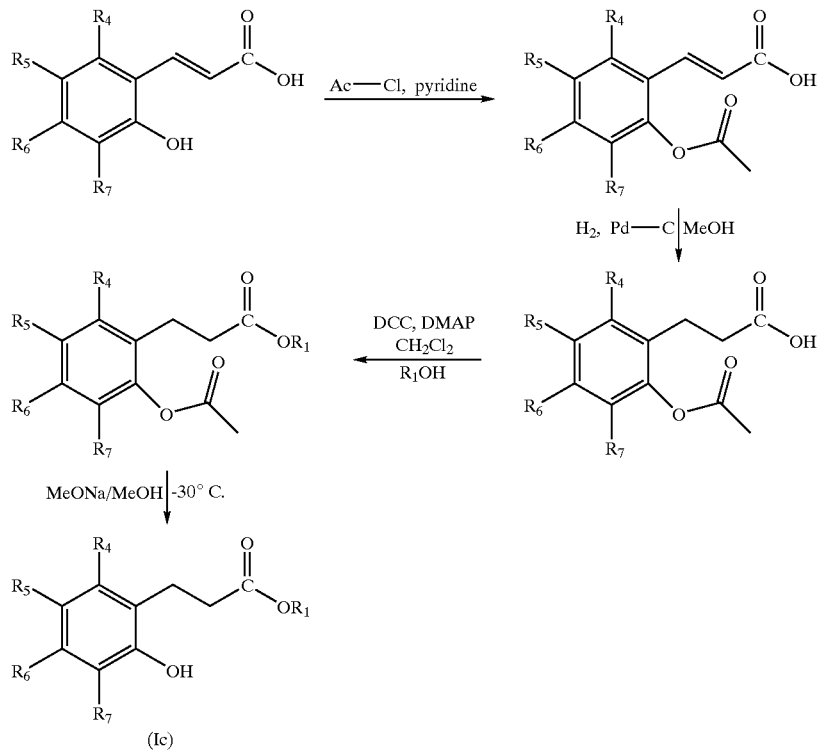

AcCl: acetyl chloride
DCC: dicyclohexylcarbodiimide
DMAP: 4-dimethylaminopyridine All the symbols used in the above diagrams have the meaning indicated in formula (I).

The compounds according to the invention lend themselves to any application requiring the prolonged-release effect of an odoriferous compound as defined above.

In these applications, the compounds of the invention can be used as such for imparting, enhancing or modifying the odor properties of the composition or product to which they are added, or as being part of a perfume formulation comprising other perfuming ingredients, solvents or adjuvants of current use in the preparation of a perfume formulation. Such perfume formulations are objects of the present invention.

The terms "perfume formulation", also sometimes simply referred to as "perfume", must be understood within the framework of the art of perfumery. In this field, these terms designate, in a general manner, a blend of odoriferous materials, perceived as having its own unique and aesthetically appropriate identity. More particularly, it is a carefully balanced blend based on a definite composition (specific ingredients and specific proportions of each of them) in which each material plays its part in achieving the overall fragrance effect. This creative and original composition is thus structurally characterized by a formulation constituted by the ingredients themselves and their relative proportions.

Therefore, a perfume formulation in the field of perfumery is not just a mixture of pleasantly smelling materials. On the other hand, a chemical reaction which constitutes a dynamic system, cannot be assimilated, as regards the reactants or the products formed, and unless otherwise specified, to a perfume formulation, even when odoriferous materials are present among the starting products, the formed products, or even both of them.

Now, apart from having a well-defined identity, a perfume or perfume formulation must meet a number of technical requirements. It must be for instance sufficiently strong, it must be diffusive, it must be persistent, and it must retain its essential fragrancing character throughout its period of evaporation.

Besides, a perfume formulation must be adapted as a function of the application for which it is intended. In particular, a perfume formulation may be designed for fine fragrance, or designed for a functional product (soap, detergent, cosmetics, etc.) which require a degree of persistence appropriate to the use for which they are intended. The formulations must also be chemically stable in the end product.

Now, these technical considerations imply that a perfume formulation may comprise other ingredients that perfuming materials, which are hereby designated as "solvents or adjuvants of current use in the preparation of a perfume formulation".

First of all, independently of whether the composition is designed for fine perfumery or for use in a technical product, a solvent system is most of the time part of the fragrance. Solvents currently used in the preparation of a perfume formulation include, but are not limited to, dipropylene glycol, diethyl phthalate, isopropyl myristate, benzyl benzoate, 2-(2-ethoxyethoxy)-1-ethanol or ethyl citrate for the most commonly used.

On the other hand, the creation of a perfume formulation intended for a functional product involves considerations both of aesthetics (how should the product smell) and of the technique of adapting the perfume to the product formulation or, as is often said, to the product base. The perfume formulation may therefore comprise "adjuvants" which can have many different functions, depending on the base which has to be perfumed. These adjuvants include for instance stabilizers and antioxidants.

Today, the range of product types and functional product formulations that are perfumed has become so extensive and subjected to such frequent changes that an approach based on a product by product basis and on the definition for each case of the adjuvants that can be used, is impractical. That is why the present application does not comprise an exhaustive list or detailed approach of the solvents or adjuvants currently used in perfume formulations. However, a skilled person in the art, i.e. and expert perfumer, is capable of choosing these ingredients as a function of the product to be perfumed and of the nature of the perfuming ingredients in the perfume formulation.

Now, the compounds of the invention, as such, or as being part of perfuming formulations can be used both in fine and functional perfumery. As for example, they can be used in applications such as a perfume, an eau de toilette or an after-shave lotion, but also in functional products, i.e. together with functional constituents of bases present in products such as shower or bath soaps or gels, foam baths or shampoos or other hair-care products, cosmetic preparations, body deodorant or air-fresheners, detergents or fabric softeners or household products. In applications such as shower or bath soaps or gels, foam baths or shampoos, a neutral or even basic pH capable or inducing hydrolysis of the ester bond and thus release of a fragrant alcohol, may be reached for instance as a result of a high dilution of the base in water.

The compounds may also be employed in applications such as detergent compositions or cleaning materials for washing the dished or various surfaces, whether intended for domestic or industrial use.

The compounds of the invention are used in a particular embodiment in functional perfumery, in applications such as liquid or solid detergents intended for the treatment of textiles and textile softeners, for which one seeks ingredients the odours of which, once imparted to the textile during washing, can be perceived by the consumer over a period of several days thereafter. The invention enables the odoriferous effect of the above-mentioned alcohols, and thus the "freshness" of the washing, to be prolonged for several days.

The compounds of the invention may be used as perfuming ingredients for the washing in all types of detergent or softening base in which these compounds are stable. By way of example, detergents of the type of those described in the patent WO 97/34986 may be used. Moreover, as softening bases one may select those described in the patents U.S. Pat. No. 4,137,180, U.S. Pat. No. 5,236,615, or EP 799 885. Other typical compositions of detergents and softeners which may be used are described in works such as Ullmann's Encyclopedia of Industrial Chemistry, vol. A8, pages 315–448 (1987) and vol. A25, pages 747–817 (1994); E. W. Flick, Advanced Cleaning Product Formulations, Noyes Publication Park Ridge, N.J. (1989); M. S. Showell (Ed.), in Surfactant Science Series, vol. 71; Powered Detergents, Marcel Dekker, New York, N.Y. (1998); Proceedings of the $4^{th}$ World Conference on Detergents: Strategies for the $21^{st}$ century, A. Cahn (Ed), AOCS Presse, Champaign (1998).

In all these applications the compounds may be used on their own, mixed together, or in the form of perfume formulations, i.e. of mixtures with other perfuming ingredients, solvents or adjuvants currently used in the preparation of perfume formulations. The nature and variety of these co-ingredients do not require a more detailed description here. In any case, this could not be exhaustive, as the person skilled in the art is able to select them on the basis of his or her general knowledge, and depending on the nature of the product to be perfumed and the required olfactory effect. These perfuming ingredients belong to classes of chemicals as varied as alcohols, aldehydes, ketones, esters, ethers, acetates, nitrites, terpene hydrocarbons, nitrogenous or sulphurous heterocyclic compounds, as well as essential oils of natural or synthetic origin. Many of these ingredients are moreover indexed in reference texts such as S. Arctander's book, Perfume and Flavor Chemicals, 1969, Montclair, N.J., USA, or its more recent editions, or in other works of a similar nature.

The proportions in which the compounds according to the invention may be incorporated into the different products mentioned above vary within an extensive range of values. These values depend on the nature of the article or product to be perfumed and the required olfactory effect, as well as on the nature of the co-ingredients in a given composition when the compounds of the invention are used in mixtures with perfuming co-ingredients, solvents or adjuvants currently used in the preparation of a perfume formulation.

By way of example one may cite typical concentrations of the order of 0.1 to 5%, or more, by weight of these compounds relative to the weight of the composition in which they are incorporated. Concentrations below these may be used when these compounds are directly applied to the perfuming of the various consumer products mentioned above.

EXAMPLES

The invention will now be described in more detail in the following examples, in which the temperatures are given in degrees Celsius, the coupling constants (J) are given in Hertz and the abbreviations have the conventional meaning in the art.

Example 1
Preparation of the Formula (I) Compounds
a) 3,7-Dimethyl-6-octenyl 2-formylbenzoate A solution of 7.50 g (50.0 mmol) 2-formylbenzoic acid, 4.88 g (40.0 mmol) 4-dimethyl aminopyridine (DMAP) and 15.60 g (100.0 mmol) citronellol in 75 ml dichloromethane was cooled in an ice bath before addition of a solution of 11.35 g (55.0 mmol) dicyclohexylcarbodiimide (DCC) in 25 ml dichloromethane for 15 min. The reaction medium was maintained with stirring at 0° for 15 min, then at 20° for 48 h. The precipitate formed during the reaction was filtered and the filtrate washed with HCl (10%, 2×) and with a saturated $Na_2CO_3$ solution (2×). The organic phase was dried over $Na_2SO_4$, concentrated and chromatographed twice ($SiO_2$, ethyl toluene/ethyl acetate 19:1 and $SiO_2$, toluene) to give 2.25 g (16%) 3,7 dimethyl-6-octenyl 2-formylbenzoate in the pure state in the form of a colourless oil.

Analytical data:
UV/V is (hexane): 288(1400), 241(8500).
IR(neat): 2960m, 2924m, 2854m, 2117m, 1774w, 1713s, 1697s, 1594m, 1577w, 1449m, 1379m, 1359w, 1346w, 1302w, 1264s, 1192m, 1162w, 1131m, 1077s, 1043w, 985w, 947w, 890w, 821m, 800w.
$^1$H-NMR(360 MHz, $CDCl_3$): 10.63(s, 1H), 8.00–7.90(m, 2H), 7.70–7.60 (m, 2H), 5.15–5.05 (m, 1H), 4.50–4.36(m, 2H), 2.12–1.92(m, 2H), 1.92–1.78 (m, 1H), 1.78–1.52 (m, 2H), 1.67(s, 3H), 1.60(s, 3H), 1.48–1.34(m, 1H), 1.34–1.17 (m, 1H), 0.98(d, J=6.3, 3H).
$^{13}$C NMR(90.6 MHz, $CDCl_3$): 192.06(d); 166.33(s); 137.10(s); 132.89(d); 132.45(s); 132.26(d); 131.46(s); 130.31(d), 128.35(d); 124.45(d); 64.49(t); 36.94(t); 35.44(t); 29.53(d); 25.70(q); 25.37(t); 19.46(q); 17.66(q).
MS(EI): 151(20), 150(15), 149(89), 140(3), 139(4), 138 (41), 137(21), 135(2), 134(17), 133(100), 132(12), 125(2), 124(5), 123(53), 122(5), 121(7), 112(2), 111(6), 110(6), 109(24), 106(4), 105(37), 104(32), 97(4), 96(15), 95(73), 94(7), 93(10), 84(7), 83(17), 82(58), 81(93), 80(9), 79(5), 78(3), 77(36), 76(17), 75(3), 74(2), 71(5), 70(26), 69(91), 68(27), 67(49), 66(2), 65(12), 57(12), 56(15), 55(46), 54(4), 53(12), 52(2), 51(17), 50(7), 43(12), 42(10), 41(98), 40(3), 39(17), 29(14), 27(11).

b) (E)-3,7-Dimethyl-2,6-octadienyl 2-formylbenzoate

A solution of 7.50 g (50.0 mmol) 2-formylbenzoic acid, 4.89 g (40.0 mmol) DMAP and 15.42 g (100.0 mmol) geraniol in 75 ml dichloromethane was cooled in an ice bath before addition of a solution of 11.37 g (55.0 mmol) DCC in 25 ml dichloromethane, for 15 min. The reaction medium was maintained under stirring at 0° for 15 min, then at 20° for 48 h. The precipitate formed during the reaction was filtered and the filtrate washed with HCl (10%, 2×) and with a saturated $Na_2CO_3$ solution (2×) and water (2×). The organic phase was dried over $Na_2SO_4$, concentrated and chromatographed ($SiO_2$, 8:2 heptane/ether) to give 2.55 g (22%) (E)-3,7-dimethyl-2,6-octadienyl 2-formylbenzoate in the pure state in the form of a colourless oil.

Analytical data:
UV/V is (hexane): 288 (1400), 241 (9000), 209 (36800).
IR (neat): 2967w, 2914m, 2853w, 1777w, 1711s, 1695s, 1594m, 1577m, 1484w, 1446m, 1376m, 1340w, 1303w, 1253s, 1191m, 1162w, 1128m, 1071s, 1040w, 963w, 924m, 890w, 819m, 799w, 748s, 699m, 639m.
$^1$H-NMR (360 MHz, $CDCl_3$): 10.63(s, 1H); 8.01–7.90(m, 2H); 7.68–7.60(m, 2H); 5.52–5.45(m, 1H); 5.13–5.05(m, 1H); 4.90(d, J=7.5, 2H); 2.18–2.03(m, 4H); 1.78(s, 3H); 1.67(s, 3H); 1.61(s, 3H).
$^{13}$C-NMR (90.6 MHz, $CDCl_3$): 192.14(d); 166.34(s); 143.48(s); 136.99(s); 132.91(d); 132.57(s); 132.23(d); 131.95(s); 130.41(d); 128.31(d); 123.63(d); 117.73(d); 62.75(t); 39.55(t); 26.26(t); 25.68(q); 17.71(q); 16.59(q).
MS (EI): 151(8), 150(3), 149(29), 137(3), 136(20), 135 (3), 134(12), 133(51), 123(4), 122(5), 121(20), 107(7), 106(4), 105(18), 104(4), 95(8), 94(9), 93(40), 92(11), 91(5), 81(10), 80(19), 79(7), 78(3), 77(20), 76(6), 70(7), 69(100), 68(60), 67(24), 65(8), 55(7), 53(12), 51(11), 50(5), 43(5), 42(4), 41(80), 39(14), 29(7), 27(9).

In the same way we prepared (Z)-3,7-dimethyl-2,6-octadienyl 2-formylbenzoate using 15.0 g (100 mmol) 2-formylbenzoic acid, 9.76 g (80 mmol) DMAP and 30.84 g (200 mmol) nerol in 150 ml dichloromethane and 22.70 g (110.0 mmol) DCC in 50 ml dichloromethane. Column chromatography ($SiO_2$, toluene) of 2×5 g of the crude product gave 1.58 g (corresponding to a total yield of 24%) of the pure product.

Analytical data:
UV/V is (hexane): 287 (1000), 278(sh, 900), 240 (6400), 232(sh, 6100), 208(sh, 27100).
IR (neat): 2964m, 2913m, 2856m, 1777m, 1710s, 1696s, 1594m, 1577m, 1483w, 1447m, 1376m, 1358w, 1347w, 1304w, 1254s, 1192m, 1162w, 1128m, 1071m, 1040m, 1010w, 983w, 923m, 894w, 819m, 799w, 748s, 713w, 700m, 688w.
$^1$H-NMR (360 MHz, $CDCl_3$): 10.63(s, 1H); 8.02–7.90(m, 2H); 7.68–7.59(m, 2H); 5.49(t, J=7.3, 1H); 5.16–5.07(m, 1H); 4.87(d, J=7.5, 2H); 2.25–2.00(m, 4H); 1.80(s, 3H); 1.67(s, 3H); 1.60(s, 3H).
$^{13}$C-NMR (90.6 MHz, $CDCl_3$): 192.17(d); 166.30(s); 143.64(s); 136.99(s); 132.91(d); 132.52(s); 132.35(s), 132.24(d); 130.41(d); 128.31(d); 123.45(d); 118.58(d); 62.49(t); 32.24(t); 26.63(t); 25.69(q); 23.55(q); 17.68(q).
MS (EI): 153(5), 151(13), 150(8), 149(60), 137(6), 136 (33), 135(6), 134(21), 133(95), 123(6), 122(7), 121(36), 108(3), 107(12), 106(4), 105(24), 104(4), 95(13), 94(14), 93(79), 92(18), 91(8), 82(3), 81(19), 80(31), 79(8), 78(3), 77(22), 76(6), 70(7), 69(100), 68(59), 67(24), 65(8), 55(5), 53(13), 51(8), 50(3), 43(5), 41(39), 39(7).

c) 2-Phenylethyl 2-formylbenzoate

A solution of 12.72 g (84.8 mmol) 2-formylbenzoic acid, 8.27 g (67.8 mmol) DMAP and 20.69 g (169.6 mmol) 2-phenylethanol in 130 ml dichloromethane was cooled in an ice bath before adding a solution of 19.25 g (93.3 mmol) DCC in 40 ml dichloromethane for 10 min. The reaction medium was maintained under stirring at 0° for 15 min, then at 20° for 48 h. The precipitate formed during the reaction was filtered and the filtrate washed with HCl (10%, 2×) and with a saturated $Na_2CO_3$ solution (2×) and with water (2×). The organic phase was dried over $Na_2SO_4$, concentrated and chromatographed ($SiO_2$, 8:2 heptane/ether) to give 2.38 g (11%) 2-phenylethyl 2-formylbenzoate in the pure state in the form of a colourless oil.

Analytical data:
UV/V is (hexane): 336 (28), 288 (1400), 241 (8400), 209 (37700).

IR (neat): 3064w, 3026w, 2953w, 2893w, 1712s, 1692s, 1593m, 1577m, 1496m, 1483w, 1465w, 1452m, 1382m, 1264s, 1253s, 1191m, 1163w, 1126s, 1075m, 1040m, 1030m, 989m, 961m, 908w, 891w, 863w, 818w, 799m, 746s, 698s.

$^1$H-NMR (360 MHz, CDCl$_3$): 10.50(s, 1H); 7.95–7.86(m, 2H); 7.66–7.57(m, 2H); 7.37–7.30(m, 2H); 7.30–7.22(m, 3H); 4.60(t, J=6.9, 2H); 3.10(t, J=6.9, 2H).

$^{13}$C-NMR (90.6 MHz, CDCl$_3$): 192.06(d); 166.17(s); 137.44(s); 137.04(s); 132.91(d); 132.35(d); 132.18(s); 130.34(d); 128.92(d); 128.65(d); 128.35(d); 126.79(d); 66.36(t); 35.08(t).

MS (EI): 236(1), 150(3), 149(27), 134(3), 133(23), 121 (3), 106(5), 105(35), 104(100), 93(2), 91(8), 79(6), 78(7), 77(18), 76(5), 65(5), 51(7), 50(3), 39(2).

This product was also prepared with a yield of 14% from 2-formylbenzoic acid and 2-bromoethylbenzene in acetone in the presence of potassium carbonate.

d) (E)-3,7-Dimethyl-2,6-octadienyl 2-acetylbenzoate

A solution of 6.49 g (39.0 mmol) 2-acetylbenzoic acid, 3.81 g (31.2 mmol) DMAP and 12.32 g (80.0 mmol) geraniol in 60 ml dichloromethane was cooled in an ice bath before adding a solution of 8.84 g (42.9 mmol) DCC in 40 ml dichloromethane for 5 min. The reaction mixture was maintained with stirring at 40° for 75 h. The precipitate formed during the reaction was filtered and the filtrate washed with HCl (10%, 2×) and with a saturated Na$_2$CO$_3$ solution (2×). The organic phase was dried (Na$_2$SO$_4$) and concentrated. The excess geraniol was distilled, and the residue chromatographed (SiO$_2$, 9:1 toluene/ethyl acetate) to give 9.08 g (78%) of the desired compound in the form of a slightly yellow oil.

Analytical data:
UV/V is (hexane): 313(sh, 200), 300(sh, 200), 282(sh, 900), 276(900), 268(1000), 228(9200).

IR(neat): 2966w, 2920m, 2856w, 1784w, 1715s, 1704s, 1673w, 1597w, 1574w, 1494w, 1484w, 1445m, 1376m, 1354m, 1263s, 1205w, 1163w, 1137m, 1126m, 1100m, 1062m, 1038w, 1006w, 955m, 931m, 886w, 834w, 799w, 761m, 731m, 708m, 696m, 661w.

$^1$H-NMR(360 MHz, CDCl$_3$): 7.90–7.84(m, 1H), 7.55 (ddd, J=7.5, 7.5, 1.2, 1H), 7.48(ddd, J=7.5, 7.5, 1.2, 1H), 7.39(dd, J=7.5, 1.6, 1H), 5.49–5.41(m, 1H), 5.13–5.05(m, 1H), 4.83(d, J=7.5, 2H), 2.53(s, 3H), 2.20–1.95(m, 4H), 1.75(s, 3H), 1.67(s, 3H), 1,60(s, 3H).

$^{13}$C NMR(90.6 MHz, CDCl$_3$): 203.01(s), 166.92(s), 143.12(s), 142.94(s), 131.95(d), 131.85(s), 129.91(d), 129.78(d), 129.09(s), 128.23(s), 126.36(d), 123.73(d), 117.75(d), 62.51(t), 39.55(t), 30.17(q), 26.31(t), 25.66(q), 17.69(q), 16.54(q).

MS(EI): 166(2), 165(23), 153(1), 150(1), 149(6), 148 (28), 147(100), 146(8), 137(3), 136(26), 135(1), 129(1), 123(3), 122(2), 121(19), 120(1), 119(1), 118(2), 109(1), 108(2), 107(6), 106(1), 105(11), 104(6), 103(1), 97(1), 96(1), 95(4), 94(11), 93(33), 92(10), 91(20), 90(2), 89(2), 85(1), 84(1), 83(1), 82(1), 81(5), 80(13), 79(6), 78(1), 77(8), 76(7), 75(1), 74(1), 71(1), 70(3), 69(46), 68(42), 67(15), 66(1), 65(4), 63(1), 59(1), 55(3), 54(1), 53(6), 52(1), 51(2), 50(2), 43(6), 42(2), 41(22), 40(1), 39(4), 29(1), 27(2).

e) 3,7-Dimethyl-6-octenyl 2-acetylbenzoate

A solution of 6.49 g (30.0 mmol) 2-acetylbenzoic acid, 3.81 g (31.2 mmol) DMAP and 12.48 g (80.0 mmol) citronellol in 60 ml dichloromethane was cooled in an ice bath before adding a solution of 8.84 g (42.9 mmol) DCC in 40 ml dichloromethane over 5 min. The reaction mixture was maintained with stirring at 40° for 75 h. The precipitate formed during the reaction was filtered and the filtrate washed with HCl (10%, 2×) and with a saturated Na$_2$CO$_3$ solution (2×). The organic phase was dried (Na$_2$SO$_4$), and the solvent evaporated. The excess citronellol was distilled (1 Torr, 60–80°), and the residue chromatographed (SiO$_2$, 9:1 toluene/ethyl acetate) and distilled (0.6 Torr, 150–155°), to give 7.43 g (63%) of 3,7-dimethyl-6-octenyl 2-acetylbenzoate in the form of a colourless oil.

Analytical data:
UV/V is (hexane): 313(sh, 100), 281(sh, 1000), 276 (1000), 229(9000).

IR(neat): 2961m, 2913m, 2872w, 2855w, 1717s, 1704s, 1597w, 1574w, 1446m (broad), 1378w, 1354m, 1264s, 1248m, 1129m, 1100m, 1064m, 1038w, 1007w, 956m, 884w, 835w, 801w.

$^1$H-NMR(360 MHz, CDCl$_3$): 7.86(dd, 3=7.5, 1.2, 1H), 7.56(ddd, J=7.5, 7.5, 1.2, 1H), 7.49(ddd, J=7.5, 7.5, 1.6, 1H), 7.40(dd, J=7.5, 1.2, 1H), 5.14–5.05(m, 1H), 4.42–4.27(m 2H), 2.54(s, 3H), 2.18–2.12(m, 2H), 1.87–1.72(m, 1H), 1.72–1.48(m, 2H), 1.67(s, 3H), 1.60(s, 3H), 1.46–1.32(m, 1H), 1.29–1.15(m, 1H), 0.95(d, J=6.3, 3H).

$^{13}$C NMR(90.6 MHz, CDCl$_3$): 202.93(s); 166.97(s); 142.92(s); 131.95(d); 131.35(s); 129.92(d); 129.70(s); 129.09(s); 126.36(d); 124.54(d); 64.25(t); 36.97(t); 35.29(t); 30.13(q); 29.49(d); 25.70(q); 25.38(t); 19.40(q); 17.65(q).

MS(EI): 166(2), 165(23), 149(12), 148(19), 147(100), 146(41), 139(2), 138(18), 137(3), 124(3), 123(28), 118(6), 110(3), 109(13), 105(7), 104(18), 96(6), 95(30), 94(2), 93(2), 91(13), 90(9), 89(5), 83(5), 82(21), 81(33), 80(3), 79(2), 77(5), 76(14), 75(3), 74(3), 71(4), 70(4), 69(26), 68(8), 67(16), 65(2), 63(2), 57(2), 56(4), 55(11), 53(3), 50(4), 43(5), 42(2), 41(15), 39(3).

f) (1R,3R,4S)-3-p-Menthanyl 2-acetylbenzoate

A solution of 11.36 g (50.0 mmol) 2-acetylbenzoic acid, 4.88 g (40.0 mmol) DMAP and 23.40 g (150.0 mmol) (−)-menthol in 80 ml dichloromethane was cooled in an ice bath before adding a solution of 11.36 g (55.0 mmol) DCC in 40 ml dichloromethane for 15 min. The reaction mixture was maintained with stirring at 40° for 70 h. The precipitate formed during the reaction was filtered and the filtrate washed with HCl (10%, 2×) then with a saturated Na$_2$CO$_3$ solution (2×). The organic phase was dried (Na$_2$SO$_4$), concentrated, chromatographed (SiO$_2$, toluene) and recrystallized in hexane to give 1.96 g (13%) (1R,3R,4S)-3-p-menthanyl 2-acetylbenzoate in the form of white crystals.

Analytical data:
M.p.: 89–91° C.
UV/V is (hexane): 315(sh, 100), 281(sh, 900), 275(1000), 229(9700).

IR(neat): 3068w, 2962m, 2951m, 2924m, 2914m, 2865m, 2847m, 1716s, 1686s, 1593w, 1576w, 1488w, 1455m, 1417w, 1385w, 1360m, 1335w, 1284m, 1272s, 1259s, 1183w, 1154w, 1139m, 1106m, 1095m, 1080w, 1064m, 1035m, 1016w, 980m, 954s, 914m, 884w, 838w.

$^1$H-NMR(360 MHz, CDCl$_3$): 7.87(dd, J=7.7, 1.4, 1H), 7.55(ddd, J=7.5, 7.5, 1.6, 1H), 7.48(ddd, J=7.5, 7.5, 1.6, 1H), 7.38(dd, J=7.5, 1.2, 1H), 4.93(ddd, J=11.0, 11.0, 4.3, 1H), 2.54(s, 3H), 2.21–2.12(m, 1H), 2.02–1.88(m, 1H), 1.78–1.67 (m, 2H), 1.63–1.44(m, 2H), 1.20–1.03(m, 2H), 1.00–0.85(m, 1H), 0.94(d, J=6.7, 3H), 0.92(d, J=7.1, 3H), 0.80(d, J=6.7, 3H).

$^{13}$C NMR(90.6 MHz, CDCl$_3$): 203.20(s), 143.20(s), 131.92(d), 129.76(d), 129.64(d), 129.26(s), 126.23(d), 75.84 (d), 47.16(d), 40.59(t), 34.25(t), 31.49(d), 30.35(q), 26.30 (d), 23.42(t). 22.02(q), 20.81(q), 16.26(q).

MS(EI): 303([M+1]$^+$, 1): 166(4), 165(37), 150(1), 149(9), 148(32), 147(100), 146(3), 139(6), 138(23), 137(2), 124(1),

123(10), 117(1), 111(1), 105(6), 104(4), 97(2), 96(5), 95(20), 94(2), 93(1), 92(1), 91(13), 90(1), 89(1), 84(1), 83(9), 82(5), 81(13), 80(1), 79(2), 78(1), 77(3), 76(4), 75(1), 71(1), 69(4), 68(1), 67(3), 65(2), 57(2), 56(1), 55(6), 54(1), 53(1), 51(1), 50(1), 43(4), 41(3), 39(1).

g) (1R,3R,4S)-3-p-Menthanyl 2-hydroxymethylbenzoate 3.78 g (12.4 mmol) monomenthyl (−)-phthalate (Fluka) was heated at reflux in 19 ml oxalyl chloride (18 eq.) for 1.5 h. The excess oxalyl chloride was distilled under vacuum. 2.75 g crude acid chloride was then diluted in 5 ml THF cooled to −8° under argon, and 0.97 g (3 eq.) $NaBH_4$ was added. The reaction mixture was maintained under stirring at 0° for 10 min and at ambient temperature for 30 min. The mixture was then poured over cold 5% $KHSO_4$ then extracted using diethyl ether. Chromatography of the crude product over silica gel (93:7 toluene/ether) yielded 1.85 g (55%) pure (1R,3R,4S)-3-p-menthanyl 2-hydroxymethylbenzoate in the form of a colourless oil.

Analytical data:

$^1$H-NMR(360 MHz, $CDCl_3$): 7.99(dd, J=7.5, 1.2, 1H), 7.52(ddd, J=7.5, 7.5, 1.6, 1H), 7.45(dd, J=7.5, 1.2, 1H), 7.38(ddd, J=7.5, 7.5, 1.6, 1H), 4.97(ddd, J=11.0, 11.0, 4.3, 1H), 4.81 and 4.73(AB of ABX, J=12.6, 7.1, 2H), 4.00(t, J=7.1, 1H, exchanged with $D_2O$), 2.13(m, 1H), 1.97(m, 1H), 1.75(m, 2H), 1.56(m, 2H), 1.14(m,1H), 0.95(d, J=6.7, 3H), 0.93(d, J=7.1, 3H), 0.81(d, J=7.1, 3H).

$^{13}$C-NMR(90.6 MHz, $CDCl_3$): 167.7(s), 142.9(s), 123.8 (d), 131.0(d), 130.5(d), 129.8(s), 127.9(d), 75.6(d), 64.8(t), 42.3(d), 40.9(t), 34.3(t), 31.5(d), 26.5(t), 23.5(t), 22.0(q), 20.8(q), 16.3(q).

MS(CI, $NH_3$): 291(1), 152(100), 135(52), 123(5), 105(10), 95(2).

h) 3,7-Dimethyl-6-octenyl 2-hydroxymethylbenzoate 5 g (16.4 mmol) monocitronellyl (+)-phthalate was heated at reflux in 25 ml oxalyl chloride (18 eq.) for 3 h. The excess oxalyl chloride was distilled under vacuum. 5.3 g crude acid chloride was then diluted in 40 ml THF cooled to −8° under argon, and 1.87 g (3 eq.) $NaBH_4$ was added. The reaction mixture was maintained under stirring at 0° for 4 h, then at ambient temperature for 16 h. The reaction mixture was then cooled again to 0°, and then 10 ml methanol was added dropwise. After 15 min, the mixture was poured over cold 5% $KHSO_4$ then extracted using cold ethyl acetate. Chromatography of the crude product over silica gel (9:1 toluene/ether) yielded 1.41 g (31%) of almost pure 3,7-dimethyl-6-octenyl 2-hydroxymethylbenzoate in the form of a colourless oil.

Analytical data:

$^1$HNMR(360 MHz, $CDCl_3$): 7.99(dd, J=7.8, 1.2, 1H), 7.52(ddd, J=7.5, 7.2, 1.2, 1H), 7.45(dd, J=7.5, 1.2, 1H), 7.37(ddd, J=7.8, 7.5, 1.2, 1H), 5.10(m, 1H), 4.78(d, J=7.2, 2H), 4.38(m, 2H), 3.96(t, J=7.2, 1H), 2.02(m, 2H), 1.81(m, 2H), 1.68(s, 3H), 1.63(m, 1H), 1.61(s, 3H), 1.41(m, 1H), 1.25(m, 1H), 0.98(d, J=6.5, 3H).

$^{13}$C-NMR(90.6 MHz, $CDCl_3$): 168.1(s), 143.0(s), 132.9 (d), 131.5(s), 131.1(d), 130.3(d), 129.3(s), 127.8(d), 124.5 (d), 64.8(t), 64.0(t), 37.0(t), 35.5(t), 29.6(d), 25.7(q), 25.4(t), 19.5(q), 17.7(q).

MS(CI, $NH_3$): 308(1, M+$NH_4^+$), 291(0.5, M+H$^+$), 174(8), 169(15), 152(100), 135(5), 105(3).

i) 2-Phenylethyl 2-hydroxymethylbenzoate 25.2 g (93 mmol) monophenylethyl (−)-phthalate was heated at reflux in 50 ml oxalyl chloride (3 eq.) for 2 h. The excess oxalyl chloride was distilled under vacuum. The crude acid chloride was then diluted in 100 ml THF cooled to 0° under argon, and 7.4 g (2 eq.) $NaBH_4$ was added. The reaction mixture was maintained under stirring at ambient temperature for 1 h, then cooled to 0° and 20 ml of methanol was added. After leaving the reaction mixture under stirring at ambient temperature for 1 h it was poured over cold 5% $KHSO_4$ then extracted using diethyl ether. Chromatography of the crude product over silica gel (9:1 toluene/ether) yielded 12.1 g (47%) 2-phenylethyl 2-hydroxymethylbenzoate containing about 9% phthalide in the form of a white solid.

Analytical data:

$^1$H-NMR(360 MHz, $CDCl_3$): 7.93(dd, J=7.5, 1.1, 1H), 7.49(ddd, J=7.5, 7.5, 1.1, 1H), 7.43(dd, 3=7.5, 1.2, 1H), 7.36–7.24(m, 6H), 5.10(m, 1H), 4.73(d, J=7.3, 2H), 4.54(t, J=6.8, 2H), 3.84(t, J=7.3, 1H), 3.08(d, J=6.8, 2H).

$^{13}$C-NMR(90.6 MHz, $CDCl_3$): 167.9(s), 143.0(s), 137.6(s), 133.0(d), 131.1(d), 130.2(d), 129.0(s), 128.9(d), 128.6(d), 127.8(d), 126.7(d), 65.9(t), 64.6(t), 35.1(t).

j) (Z)-3-Hexenyl 2-hydroxymethylbenzoate 1 g (4.03 mmol) monohexenyl phthalate was heated at reflux in 6 ml oxalyl chloride (17.3 eq.) for 1.5 h. The excess oxalyl chloride was distilled under vacuum. The crude acid chloride was then diluted in 10 ml dichloromethane cooled to 0° under argon, and introduced dropwise on a solution of 2.07 g (2 eq.) nBuNBH$_4$ in 10 ml dichloromethane. The reaction mixture was maintained under stirring at 0° for 2.5 h. The mixture was then poured over 5% $KHSO_4$ and cold ethyl ethyl acetate, and extracted. Chromatography of the crude product over silica gel (85:15 cyclohexane/AcOEt) yielded 0.3 g (32%) (Z)-3-hexenyl 2-hydroxymethylbenzoate containing about 10% phthalide, in the form of a colourless oil.

Analytical data:

$^1$H-NMR(360 MHz, $CDCl_3$): 8.00(dd, J=7.6, 1.1, 1H), 7.52(ddd, J=7.5, 7.5, 1.2, 1H), 7.45(dd, J=7.5, 1.2, 1H), 7.37(ddd, J=7.6, 7.5, 1.2, 1H), 5.55(m, 1H), 5.41(m, 1H), 4.77(broad s, 2H), 4.34(t, J=6.9Hz), 3.89(broad signal, 1H), 2.54(dd, J=13.9, 6.9, 2H), 2.10(dq, J=13.9, 7.5, 2H), 0.97(t, J=7.5, 3H).

$^{13}$C-NMR(90.6 MHz, $CDCl_3$): 168.0(s), 143.0(s), 134.9 (d), 133.0(d), 131.1(d), 130.3(d), 129.1(s), 127.8(d), 123.6 (d), 65.0(t), 64.8(t), 26.8(t), 20.7(t), 14.2(q).

MS(CI, $NH_3$): 252(2, M+$NH_4^+$), 235(10, M+H$^+$), 213(5), 152(100), 135(10), 119(2), 105(5), 94(1).

k) (E)-3,7-Dimethyl-2,6-octadienyl 2-hydroxymethylbenzoate

A solution of 10.0 g geraniol (64.9 mmol). 9.6 g phthalic anhydride (1 eq.). 3.5 g diisopropyl-ethylamine (DIEA) (1 eq.) and 0.79 g 4-dimethylaminopyridine (0.1 eq.), in 130 ml dichloromethane was maintained under stirring at ambient temperature for 24 h. The dichloromethane was concentrated then taken up in ethyl acetate, washed with 5% $KHSO_4$, then with water, dried over $Na_2SO_4$ and finally evaporated to obtain 19.0 g of a colourless oil. 5 g of the monophthalate thus obtained (16.6 mmol) was dissolved in 50 ml dichloromethane. 2.35 g DIEA (1.1 eq.) was added, then, at 5°, 2.26 g isobutyl chloroformiate (1 eq.) was added dropwise. The mixture was maintained under stirring at ambient temperature for 3 h, then 200 ml dichloromethane was added. The organic phase was then washed with water and dried over $Na_2SO_4$. The solvent was evaporated to obtain 6.34 g of slightly yellow oil. 1 g of this product (2.49 mmol) was then added dropwise to a solution at −20° of 0.38 g sodium borohydride (4 eq.) in 10 ml ethanol. After reacting for 30 min, the reaction medium was poured over a cold mixture of ethyl acetate and 5% $KHSO_4$. The organic phase was washed with water, dried over $Na_2SO_4$ then evaporated. The product was purified by chromatography over silica (8:2 cyclohexane/AcOEt). 0.36 g of a colourless oil was obtained with a yield of 50%.

$^1$H-NMR(360 MHz, CDCl$_3$): 8.01(dd, J=7.5, 1.1, 1H), 7.51(ddd, J=7.5, 7.5, 1.1, 1H), 7.44(dd, J=7.5, 1.1), 7.37 (ddd, J=7.5, 7.5, 1.1, 1H), 5.51–5.44(m, 1H), 5.13–5.06(m, 1H), 4.86(d, J=7.0, 2H), 4.77(d, J=6.6, 2H), 3.93(t, J=7.0, 1H), 2.18–2.04(m, 4H), 1.78(s, 3H), 1.68(s, 3H), 1.61(s, 3H).

$^{13}$C-NMR(90.6 MHz, CDCl$_3$): 168.1(s), 143.1(s), 142.9(s), 132.9(d), 131.9(s), 131.2(d), 130.4(d), 129.3(s), 127.8(d), 123.7(d), 117.9(d), 64.8(t), 62.3(t), 39.6(t), 26.3(t), 25.7(q), 17.7(q), 16.6(q).

MS(CI, NH$_3$): 306(M+NH$_4^+$, 3), 289(M+H$^+$, 1), 107 (100), 152(35), 137(45).

l) 1-p-Menthen-8-yl 2-hydroxymethylbenzoate

A solution of 14.8 g phthalic anhydride (100 mmol), 15.4 g α-terpineol (100 mmol) and 1.22 g 4-dimethylaminopyridine (10 mmol) was brought at reflux in 70 ml pyridine, over 16 h. 20 ml water was then added and brought at reflux for a further 20 min. The water and the pyridine were evaporated then taken up in ethyl acetate. Washing was performed with 5% KHSO$_4$ then with brine, drying over Na$_2$SO$_4$ then the solvent was evaporated to collect 16.9 g of a light brown oil. The residual pyridine and α-terpineol were eliminated by distillation in a bulb-to-bulb distillation apparatus before purifying over silica gel (9:1 cyclohexane/ethyl acetate and 1% AcOH) to obtain 9.1 g of a light brown oil. 3 g of the α-terpenyl monophthalate thus obtained (9.9 mmol) was dissolved in 30 ml dichloromethane and 1.4 g DIEA was added. The mixture was cooled to 0°, then 1.35 g isobutyl chloroformate (9.9 mmol) was added dropwise and allowed to react at 0° for 1 h then at ambient temperature for 3 h. After addition of 75 ml dichloromethane, the mixture was washed 3 times with water then dried over sodium sulphate. The filtered dichloromethane solution was used for the latter stage. 0.6 g sodium borohydride (1.6 eq.) then 3 ml methanol was added dropwise. After 18 h at ambient temperature the reaction medium was poured over a cold mixture of ethyl acetate and 5% KHSO$_4$ under vigorous stirring. The organic solution was washed with brine, then dried over Na$_2$SO$_4$. The crude product was purified by chromatography over silica (90/10 cyclohexane/ethyl acetate). 1.65 g of very light brown oil was obtained with a yield of 17% in the 3 stages.

Analytical data:

$^1$H-NMR(360 MHz, CDCl$_3$): 7.91(dd, J=7.5, 1.2, 1H), 7.49(ddd, J=7.8, 7.5, 1.2, 1H), 7.41(dd, J=7.5, 1.2, 1H), 7.36(ddd, J=7.8, 7.5, 1.2, 1H), 5.40(broad s, 1H), 4.73(d, J=7.3, 2H), 4.08(t, J=7.3, 1H), 2.23(m, 1H), 2.15–1.81(m, 5H), 1.67(s, 3H), 1.61(s, 3H), 1.58(s, 3H), 1.41(m, 1H).

$^{13}$C-NMR(90.6 MHz, CDCl$_3$): 167.5(s), 142.7(s), 134.1(s), 132.5(d), 131.1(s), 131.0(d), 130.5(d), 127.8(d), 120.2(d), 86.9(s), 65.0(t), 43.0(d), 30.9(t), 26.5(t), 24.1(t), 23.5(q), 23.3(q).

MS(CI, NH$_3$): 289(M+H$^+$, 5), 170(100), 152(20), 137 (10).

m) (1'R,E)-1,2,2-Trimethyl-4-(2',-2',-3'-trimethyl-3'-cyclopenten-1'-yl)-3-butenyl 2-hydroxymethylbenzoate 1.7 ml diisopropylethylamine (10 mmol) and 61 mg 4-dimethylaminopyridine (0.5 mmol) were added to a solution of 2.22 g polysantol (10 mmol) and 1.48 g phthalic anhydride (10 mmol) in 20 ml dichloromethane. The mixture was maintained under stirring for 72 h, then after adding ethyl acetate it was washed with 5% KHSO$_4$ and with brine. After drying over Na$_2$SO$_4$ and evaporating the solvents a brown oil was collected, used as for the following stage. 0.3 ml ethyl chloroformate (3.1 mmol) was added at −10° to a solution of 1 g crude monophthalate (2.7 mmol) and 1.4 ml triethylamine (10 mmol) in methyl-tert-butyl ether (MTBE) (50 ml), and the mixture was maintained at this same temperature for 1 h under stirring. The mixture was then filtered over Celite and rinsed with 50 ml MTBE. The recovered filtrate was cooled to −10° and 420 mg NaBH$_4$ (10.8 mmol) was added. Ethanol was then added dropwise over a period of 30 min. After leaving to react for 1 h the reaction mixture was poured rapidly over a mixture of ethyl acetate and 5% KHSO$_4$ in water, the whole at 0° under vigorous stirring. The organic phase was dried over Na$_2$SO$_4$ then evaporated to collect a yellow oil which was chromatographed over silica gel (90/10 cyclohexane/ethyl acetate) to obtain 0.44 g (46%) of slightly yellow oil.

Analytical data:

$^1$H-NMR(360 MHz, CDCl$_3$): 8.01(~d, J=7.7, 1H), 7.58 (~dd, J=7.5, 1H), 7.45(~d, J=7.5, 1H), 7.38(~dd, J=7.7, 1H), 5.52(m, 2H), 5.23(m, 1H), 5.03(q, J=6.3, 1H), 4.78(m, 2H), 4.04 and 4.02(2t, J=7.3, 1H), 2.37(m, 1H), 2.23(m, 1H), 2.08(m, 1H), 1.60(broad signal, 3H), 1.28(d, J=6.3Hz, 3H), 1.12(broad s, 6H), 0.94 and 0.91(2s, 3H), 0.74 and 0.71(2s, 3H).

$^{13}$C-NMR(90.6 MHz, CDCl$_3$): 167.5(2s superimposed), 148.1(2s), 143.1(2s), 136.2(2d), 132.9(d), 131.0(d), 130.4 (d), 129.9(d), 129.7(2s), 127.8(d), 121.5(d), 78.3 and 78.2 (2d), 64.9(t), 54.4(d), 48.1(2s), 40.0(s), 35.6(s), 25.4 and 25.3(2q), 24.1(q), 23.7(q), 23.4(q), 20.5 and 20.4(2q), 15.4 and 15.3(2q), 12.7(q).

MS(CI, NH$_3$): 374(4, M+NH$_4^+$), 357(2, M+H$^+$), 222(10), 205(100), 170(40), 152(10).

n) (E)-3,7-Dimethyl-2,6-octadienyl dihydrocoumarate

Some ortho-coumaric acid was acetylated under conventional conditions to obtain ortho-acetyl coumaric acid with a yield of 49% after recrystallization. 5.54 g (26.9 mmol) o-acetyl coumaric acid was then hydrogenated for 4 h in 50 ml methanol using 0.5 g 10% Pd—C to give 5.45 g (97%) o-acetyl dihydrocoumaric acid in the form of a white solid.

A mixture of 0.8 g (3.85 mmol) of this acid, 0.6 g (1 eq.) geraniol, 0.87 g (1.1 eq.) dicyclohexylcarbodiimide and 47 mg (0.1 eq.) 4-dimethylaminopyridine was maintained under stirring in 10 ml dichloromethane for 24 h. The reaction mixture was filtered, then diluted with ethyl acetate and washed successively with 5% KHSO$_4$, 5% NaHCO$_3$, and with brine. Following chromatography over silica gel (95:5 cyclohexane/ethyl acetate) 0.62 g (58%) geranyl o-acetyl dihydrocoumarate was obtained.

The acetyl was deprotected at −15° in a mixture of 4·eq. MeONa in methanol (30 ml/mmol) in 3 h. Diethyl ether was added, washing was performed with 5% KHSO$_4$, drying with 5% Na$_2$SO$_4$, and the solvent was evaporated. The yield was 27%.

Analytical data:

$^1$H-NMR(360 MHz, CDCl$_3$): 7.10(m, 2H), 6.86(m, 2H), 5.29(tq, J=7.4, 1.2, 1H), 5.07(tq, J=6.6, 1.2, 1H), 4.60(d, J=7.4, 1H), 2.90(t, J=6.5, 2H), 2.71(t, J=6.5, 2H), 2.06(m, 4H), 1.67(broad s, 6H), 1.59(broad s, 3H).

$^{13}$C-NMR(90.6 MHz, CDCl$_3$): 175.7(s), 154.4(s), 142.9(s), 131.9(s), 130.6(d), 128.0(d), 127.4(s), 123.7(d), 120.8(d), 117.8(d), 117.3(d), 62.2(t), 39.5(t), 35.3(t), 29.7(t), 26.3(t), 25.7(q), 24.7(t), 22.7(t), 17.7(q), 16.5(q).

o) (Z)-3-Hexenyl dihydrocoumarate 2.08 g (10 mmol) o-acetyldihydrocoumaric acid, 1.0 g (10 mmol) (Z)-3-hexenol, 2.06 g (1 eq.) dicyclohexylcarbodiimide and 70 g (0.057 eq.) 4-dimethyl-aminopyridine were stirred into 40 ml dichloromethane for 16 h. The mixture was subsequently filtered then diluted using ethyl acetate, then washed successively with 5% KHSO$_4$, 5% NaHCO$_3$, and with brine. Chromatography of the product over silica gel (9:1 cyclohexane/ethyl acetate) yielded 1.78 g (61%) (Z)-

3-hexenyl o-acetyl dihydrocoumarate. 100 mg (0.34 mmol) of this product was then deacetylated by reacting with 100 μl 5.4 M MeONa in 10 ml methanol for 1 h at −10°. Following conventional treatment, 80 mg (94%) (Z)-3-hexenyl dihydrocoumarate was obtained in the form of a colourless oil.

Analytical data:

$^1$H-NMR(360 MHz, CDCl$_3$): 7.08(m 2H), 6.86(m, 2H), 5.47(m, 1H), 5.26(m, 1H), 5.41(m, 1H), 4.08(t, J=7.1, 2H), 2.90(m, 2H), 2.70(m, 2H), 2.34(dt, J=13.8, 7.1, 2H), 2.01 (dq, J=15.0, 7.6, 2H), 0.94(t, J=7.6, 3H).

$^{13}$C-NMR(90.6 MHz, CDCl$_3$): 175.6(s), 154.3(s), 134.8 (d), 130.5(d), 128.0(d), 127.3(s), 123.4(d), 120.8(d), 117.1 (d), 64.8(t), 35.1(t), 26.6(t), 24.7(t), 20.6(t), 14.2(q).

MS(ESI): 248.9(100, M+H$^+$), 167.2(75).

p) (Z)-3-Hexenyl 3-endo-hydroxymethyl-bicyclo[2.2.1] hept-5-ene-2-endo-carboxylate A mixture of 2 g (20 mmol) (Z)-3-hexenol, 3.28 g (20 mmol) bicyclo[2.2.1]hept-5-ene-anhydride-2,3-endo-dicarboxylic, 3.5 ml (20 mmol) diisopropylethylamine and 61 mg (0.5 mmol) 4-dimethylaminopyridine in 40 ml dichloromethane was maintained under stirring at ambient temperature for 24 h. This was then diluted in ethyl acetate and washed using with 5% KHSO$_4$ and brine. 5.1 g (97%) of a pale yellow solid, i.e. (Z)-3-hexenyl 3-endo-carboxy-bicyclo[2.2.1]hept-5-ene-2-endo-carboxylate, was obtained.

A mixture of 5.1 g (19.3 mmol) of this monoacid and 3.5 ml (40 mmol) oxalyl chloride was maintained under stirring for 2 h at ambient temperature. The excess oxalyl chloride was then evaporated and 40 ml dichloromethane was added. After adding 6.2 g (1.2 eq.) tetrabutylammonium borohydride, the reaction mixture was maintained under stirring for 2 h. The mixture was then poured into cold 5% KHSO$_4$ and after extraction of the product from cold ethyl acetate, 4.8 g (99%) of a pale yellow oil was obtained. Rapid filtration over silica gel (60:40 cyclohexane/ethyl acetate) yielded 1.6 g (32%) (Z)-3-hexenyl 3-endo-hydroxymethyl-bicyclo[2.2.1]hept-5-ene-2-endo-carboxylate in the form of a pale yellow oil.

Analytical data:

$^1$H-NMR(360 MHz, CDCl$_3$): 6.22(dd, J=5.6, 2.5, 1H), 6.10(dd, 7=5.6, 2.7, 1H), 5.52(m, 1H), 5.31(m, 1H), 4.05(m, 2H), 3.49(dd, J=11.6, 5.7, 1H), 3.42(dd, J=11.6, 8.7, 1H), 3.16(s, 1H), 3.14(m, 1H), 2.90(broad signal, 1H), 2.69(m, 1H), 2.38(m, 2H), 2.07(m, 2H). 1.39(m, 2H), 0.98(t, J=7.6, 3H).

$^{13}$C-NMR(90.6 MHz, CDCl$_3$): 174.6(s), 136.0(d), 134.7 (2d superimposed), 123.8(d), 64.2(t), 64.0(t), 48.8(t), 47.33 and 47.30(2d), 46.4(d), 45.9(d), 26.7(t), 20.7(t), 14.2(q).

MS(CI, NH$_3$): 268(35, M+NH$_4^+$), 251(100, M+H$^+$), 186 (5), 168(40), 151(5), 136(5),119(2), 106(2).

Example 2

Tests in a Basic Medium

A number of tests were conducted at different pH values on compounds of the invention to test the hydrolysis of the ester function in accordance with the following general methods.

General Methods a) At t=0, 10 ml of a 0.001 M solution of compound of the invention in dioxane was added rapidly to 40 ml of a buffer solution (7:1 water/dioxane) at pH 7, containing Cremophor RH-40 (BASF) to prevent emulsion. The buffer solution was prepared by dissolving two tablets of borate buffer (Fluka) in a mixture of 175 ml water and 25 ml dioxane. Hydrolysis was followed at ambient temperature until the reaction was complete by photometry by recording the optical absorption of the solution within a wavelength range of 260 to 360 nm at discrete time intervals and at a scanning rate of 960 nm/min.

b) Buffer solutions at pH 7 and 9.2 respectively were prepared by dissolving two tablets of borate or phosphate buffer (Fluka) in a mixture of 175 ml water and 25 ml dioxane or acetonitrile. 70 to 100 mg of compound of the invention was dissolved in 50 ml dioxane or acetonitrile and 0.3 ml of this solution was added to 1.2 ml of the buffer solution (pH 7 or 9.2). The mixture was immediately injected in a HPLC (high-pressure liquid chromatography) apparatus (at t=0) and eluted at 1 ml/min with a water/acetonitrile gradient varying between 70:30 and 20:80 (for 20 min) over an inverse-phase column (Macherey-Nagel Nucleosil 100-5 C 18, 250×4 mm). The sample, which was temperature-regulated to 20°, was re-injected every 30 min or every hour.

Using at least one of the two methods cited (HPLC or photometry), hydrolysis of the following compounds with release of a fragrant alcohol, under the above-mentioned pH conditions, was thus verified: 3,7-dimethyl-6-octenyl 2-formylbenzoate, (E)-3,7-dimethyl-2,6-octadienyl 2-formylbenzoate, (Z)-3,7-dimethyl-2,6-octadienyl 2-formyl-benzoate, 2-phenylethyl 2-formylbenzoate, (E)-3, 7-dimethyl-2,6-octadienyl 2-acetylbenzoate, 3,7-dimethyl-6-octenyl 2-acetylbenzoate, (1R,3R,4S)-3-p-menthanyl 2-acetylbenzoate, (1R,3R,4S)-3-p-menthanyl 2-hydroxymethylbenzoate, 3,7-dimethyl-6-octenyl 2-hydroxymethylbenzoate, 2-phenylethyl 2-hydroxymethyl-benzoate, (Z)-3-hexenyl 2-hydroxymethyl-benzoate, (E)-3, 7-dimethyl-2,6-octadienyl 2-hydroxy-methylbenzoate, 1-p-menthen-8-yl 2-hydroxymethylbenzoate, (1'R,E)-1,2,2-trimethyl-4-(2',2',3'-trimethyl-3'-cyclopenten-1'-yl)-3-butenyl 2-hydroxymethyl-benzoate, (Z)-3-hexenyl dihydrocoumarate, (E)-3,7-dimethyl-2,6-octa-dienyl dihydrocoumarate, and (Z)-3-hexenyl 3-endo-hydroxymethyl-bicyclo[2.2.1]hept-5-ene-2-endo-carboxylate.

Example 3

Test on Textiles

A number of tests were conducted on compounds of the invention to test the hydrolysis of the latter following a washing cycle on a device of the Linitest® type.

0.144 ml of a solution (10% in ethanol) of a compound of the invention or respectively 0.072 ml of a solution (10% in ethanol) of the corresponding free alcohol (roughly corresponding to the equivalent molar quantity) were added to 1.8 g of an unperfumed textile softener containing Esterquats (Stepantex® and Stepanquat®) of the following composition:

| Ingredients | % by weight |
| --- | --- |
| Stepantex ® VS90 or VHR 90* | 16.7 |
| Stepanquat ® F* | 0.4 |
| 1% colorant solution** | 0.3 |
| Water | 82.6 |
| Total | 100.0 |

*Source: Stepan, France
**Sandolan Milling Blue N-LN180; source: Clariant, Switzerland Linitest® Washing Method A standard cotton towel (28×28 cm) is placed in a Linitest® 600-ml stainless steel container. 1.8 g standard non-perfumed detergent base (for example Henkel, ECE Colour Fastness Test Detergent 77) and 400 ml cold tap water are added. The closed containers are placed in the Linitest® machine (Heraeus) and then left in a bath at 44° for 20 min under stirring. The towels are then removed and rinsed twice in a beaker, each time with 600 ml cold tap water. Rinsing with the softener is then performed in a beaker containing 600 ml cold water with 1.8 g of the softener containing in one case one of the precursor compounds of the invention (test A), and in the other case the corresponding free alcohol (test B). The towel is agitated for 5 min then wrung out by hand. Weighing is performed to ensure the same quantity of residual water in all the cloths so as not to bias the comparison between precursors and free alcohols.

Each test was performed twice. A total of 11 panellists compared, in a blinding test, the different towels still wet after washing, then dry after 1 and 6 days respectively. To avoid contamination, the dry towels were kept in large, closed crystallising dishes between evaluations. Each panellist indicated the intensity of the odour of each sample on a scale of 1 (no odour) to 10 (very strong odour), and the sample preferred between test A (precursor) and test B (free alcohol).

According to the procedure described above, 3,7-dimethyl-6-octenyl 2-formylbenzoate (I) (test A) was compared with citronellol (test B), (E)-3,7-dimethyl-2,6-octadienyl 2-formylbenzoate (II) (test A) was compared with geraniol (test B), a mixture of (E and Z)-3,7-dimethyl-2,6-octadienyl 2-formylbenzoate (III) (test A) was compared with a mixture of geraniol and nerol (test B), 2-phenylethyl 2-formylbenzoate (IV) (test A) was compared with 2-phenylethanol (test B), (E)-3,7-dimethyl-2,6-octadienyl 2-acetylbenzoate (V) (test A) was compared with geraniol (test B), and 3,7-dimethyl-6-octenyl 2-acetylbenzoate (VI) (test A) was compared with citronellol (test B).

The following table summarizes the results of the panel: each panellist compared a precursor according to the invention to the corresponding free alcohol, indicating on the one hand the odor intensity of each test on a scale of 1 to 10; the table gives the calculated average intensity for each sample; and on the other hand the preference of the panellist for test A or test B, the number in brackets corresponding to the number of panellists preferring the respective sample.

| Product | Wet towel | Dry towel (1 day) | Dry towel (6 days) |
|---|---|---|---|
| 3,7-Dimethyl-6-octenyl 2-formylbenzoate (I) | 6.1 (3) | 3.8 (10) | 5.3 (10) |
| Citronellol | 6.4 (8) | 2.5 (1) | 2.9 (1) |
| 3,7-Dimethyl-2,6-octadienyl 2-formylbenzoate (II) | 7.4 (9) | 6.1 (10) | 4.3 (9) |
| Geraniol | 5.0 (2) | 3.4 (1) | 2.3 (2) |
| (E and Z)-3,7-Dimethyl-2,6-octadienyl 2-formylbenzoate (III) | 4.9 (8) | 3.8 (9) | 5.5 (10) |
| Geraniol/Nerol | 5.3 (3) | 3.3 (2) | 2.9 (1) |
| 2-Phenylethyl 2-formyl-benzoate (IV) | 5.4 (5) | 4.7 (9) | 5.2 (10) |
| Phenylethanol | 5.1 (6) | 3.9 (2) | 2.6 (1) |
| (E)-3,7-Dimethyl-2,6-octadienyl 2-acetylbenzoate (V) | 5.0 (7) | 2.8 (5) | 4.5 (11) |
| Geraniol | 4.5 (4) | 2.6 (4) | 3.3 (0) |
| 3,7-Dimethyl-6-octenyl 2-acetylbenzoate (VI) | 3.5 (3) | 2.5 (7) | 3.9 (7) |
| Citronellol | 7.4 (8) | 2.3 (4) | 2.7 (4) |

It was thus observed that, in the majority of cases, the average intensity determined by the panellists diminished when going from the wet towels to the dry ones (1 day). Two different behaviours are then observed, for the free alcohol and the precursor, by comparing the intensity evaluated after 1 and 6 days on the dry linen. Whereas generally the intensity of the free alcohol diminishes, that of the precursor increases. Moreover although, on wet washing, the odour of the free alcohol has often been perceived as being more intense than that of the alcohol released from the compounds of the invention, on dry washing this effect is reversed, and the intensity of the alcohol released by the products of the invention (test A) was perceived as more intense than that of the free alcohol (test B). This effect very clearly reveals that the desired aim was achieved when using the compounds of the invention. Furthermore, the majority of the panellists preferred the dry sample originating from test A (precursor), after as little as 1 day. After 6 days this effect was even more pronounced, when a very large majority of the panellists (between 7 and 11 panellists out of 11) preferred the sample corresponding to the precursor.

Example 4

Tests on Textiles

A number of tests were conducted on compounds of the invention to test the hydrolysis following a washing cycle in a washing machine.

Method of Washing in a Washing Machine

About 1 kg of standard towels measuring 28×28 cm were washed at 40° in a washing machine (Miele, Deluxe electronic model W724) without prewashing, using 50 g of a standard base detergent (for example Henkel, ECE Colour Fastness Test Detergent 77) and 50 g of a currently available unperfumed softener containing Esterquats.

The textile softening base was of the following composition:

| Ingredients | % by weight |
|---|---|
| Mixture of HEQ-Esterquat*/fatty acid $C_{16}$–$C_{18}$ (6:1) | 14.00 |
| Tallowyl ethoxylate from coconut 20EO | 0.75 |
| Tallowyl alcohol | 0.75 |
| Water | 84.50 |
| Total | 100.00 |

*2,3-di($C_{16}$–$C_{18}$-acyloxy)propyltriethylammonium chloride

In two separate tests, towels were treated in accordance with this general method using as the additive of the textile softener, respectively one of the compounds of the invention (0.8% by weight) in test A and free alcohol (0.3% by weight) in test B. The two groups of towels were subjected to a blind test evaluation on their removal from the washing machine and 24 h later.

Following this procedure, 3,7-dimethyl-6-octenyl 2-formylbenzoate (test A) was compared with citronellol (test B), (E)-3,7-dimethyl-2,6-octadienyl 2-acetylbenzoate (test A) was compared with geraniol (test B), 2-phenylethyl 2-hydroxymethylbenzoate (test A) was compared with 2-phenylethanol (test B), and (E)-3,7-dimethyl-2,6-octadienyl 2-hydroxymethylbenzoate (test A) was compared with geraniol (test B).

Whereas, on wet fabrics, the towels treated in test B seemed more odoriferous than those treated in test A, 24 h after the wash the latter proved to develop a much more intense odour than those in test B, and the odour persisted for several days after the wash.

Example 5

Test on Textiles

Two groups of standard terry towels were treated separately and in an identical way as described in Example 4, by adding 0.8% (E)-3,7-dimethyl-2,6-octadienyl 2-formylbenzoate in test A and 0.13% geraniol in test B to the softening base. The towels were evaluated under blind conditions by 40 panellists in a triangular test, 20 of whom had the cloths from test A as the sole sample, and 20 those from test B. On wet fabrics, 30 of the 40 panellists correctly distinguished between the samples. Furthermore, 20 of these 30 people preferred the geraniol (test B), and 26 judged it to be the stronger. After 24 h, the triangular test was repeated on dry towels. This time, 31 of the 40 panellists distinguished correctly between the samples, and 29 of the 31 preferred the (E)-3,7-dimethyl-2,6-octadienyl 2-formylbenzoate (test A). 27 found the test-A sample to be the more powerful.

Example 6

Ironing Test on Textiles

General Method of Treating the Textiles

Washing tests were conducted on a total weight of washing of 1.5 kg, including 5 100%-cotton pillowcases (65×65 cm) and 4 100%-cotton towels (87 cm×43 cm). The fabrics were washed at 40° in a washing machine (Miele, Deluxe electronic model W724), without prewashing, using 50 g of a standard detergent base (for example Henkel, ECE Colour Fastness Test Detergent 77) and 50 g of unperfumed softener containing Ester Quats (Stepantex®).

The textile softener base used was of the following composition:

| Ingredients | % by weight |
| --- | --- |
| Stepantex ® VS90* | 16.5 |
| CaCl$_2$ (10% in solution) | 0.2 |
| Colorant 1% solution* | 0.3 |
| Water | 83.0 |
| Total | 100.0 |

*see Example 3

In the 4 independent tests, the pillow cases were washed following the method indicated above with the base containing 0.3% precursor substances according to the invention, that is to say, 2-phenylethyl 2-formylbenzoate (A), 3,7-dimethyl-6-octenyl 2-acetyl-benzoate (B), or (E)-3,7-dimethyl-2,6-octadienyl 2-acetylbenzoate (C). The pillow cases were left in the open air to dry. After 24 h, the cases were ironed using a Philips Excel Plus Steam iron, and the perfuming effect following the ironing operation was evaluated by a panel of experts on a blind test. It then emerged very clearly that the perfume corresponding to the fragrant alcohol present in each of the precursors was perceived in a significant manner when released by the action of heat and/or of the steam produced by the iron. Precursor A produced the most pronounced odoriferous effect, followed by C and then B.

What is claimed is:
1. A perfume formulation comprising, together with other perfuming ingredients, solvents or adjuvants of current use in the preparation of a perfume formulation, an active perfuming ingredient of the formula (Ib)

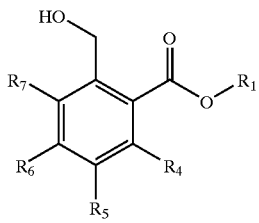

(Ib)

in which R1 represents a radical belonging to a fragrant alcohol of the formula R1OH, comprising at least four carbon atoms, m and n define whole numbers within the range 0 to 2 such that the sum m+n is equal to 1 or 2, each of the symbols R2, R4, R5, R6, R7, taken independently, represents a hydrogen atom, a C1 to C4 straight-chain or branched hydrocarbon radical, saturated or unsaturated, optionally substituted,
or an active perfuming inaredient of formula (I)

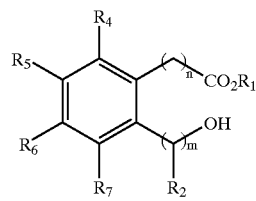

(I)

in which, m and n define whole numbers within the range 0 to 2 such that the sum m+n is equal to 1 or 2, each of the symbols R2, R4, R5, R6, R7, taken independently, represents a hydrogen atom, a C1 to C4 straight-chain or branched hydrocarbon radical, saturated or unsaturated, optionally substituted, and in which R$_1$ represents a radical belonging to a fragrant alcohol of the formula R$_1$OH and is selected from the group consisting of anisyl alcohol, fenchyl alcohol, cinnamic alcohol, 9-decen-1-ol, penethylol, citronellol (3,7-dimethyl-6-octen-1-ol), 3-methyl-5-phenyl-1-pentanol, Mayol® (7p-menthan-1-ol), dihydromyrcenol (2,6-dimethyl-oct-7-ene-2-ol), alpha-ionol, tetrahydroionol, geraniol [(E)-3,7-dimethyl-2,6-octadien-1-ol], nerol (Z)-3,7-dimethyl-2-6-octadien-1-ol, (Z)-3-hexen-1-ol, 1-hexanol, 2-hexanol, 3,3,5-trimethylhexanol, 3,4,5,6,6-pentamethyl-heptan-2-ol, 5-ethyl-2-nonanol, (Z)-6-nonenol, 6,8-dimethyl-2-nonanol, 2,6 nonadien-1-ol, borneol, 1-octen-3-ol, 4-cyclohexyl-2-methyl-2-butanol, 6-ethyl-3-methyl-5-octen-1-ol, 3,7-dimethyl-oct-3,6-dienol, 7-methoxy-3,7-dimethyl-octan-2-ol, methyl-4-phenyl-2-butanol, 2 methyl-1-phenyl-2-propanol, 1-phenylethanol, 2 phenylethanol, 2-phenylpropanol, 3 phenylpropanol, 2 methyl-5-phenylpentanol, 2-methyl-4-phenylpentanol, 3-methyl-5-phenylpentanol, cyclomethyl-citronellol, decanol, dihydroeugenol, 8-p-methanol, 3,7 dimethyl-1-octanol, 2,6-dimethyl-2-heptanol, dodecanol, octanol, undecanol, 4 methyl-3-decen-1-ol, eugenol, Florol® (tetrahydro-2-isobutyl-4-methyl-4(2H)-pyranol, 2-phenoxyethanol, isoeugenol, linalol, Tarragol® (2 methoxy-4-propyl-1-cyclohexanol, vanillin, ethyl-vanillin, anethol, farnesol, cedrenol, menthol, p-menth-8-en-3-ol, 3,3,5-trimethyl-cyclohexanol, 2,4,6-trimethyl-3-cyclohexenyl-methanol, 4-(1-methylethyl) cyclohexyl-methanol, terpineol, tetrahydromugol, 3,7 dimethyl-3-octanol, Polysantol® [(E)-3,3-dimethyl-5-(2',2',3'-trimethyl-3'-cyclopenten-1-yl)-4-penten-2-ol, 2,2,6-trimethyl-alphapropyl-cyclohexane propanol, 5-2,2,3-trimethyl-3-cyclopentyl)-3-methylpentan-2-ol, 3-methyl-5-(2,2,3-trimethylcyclopent-3-enyl)pent-4-en-2-ol, 2 ethyl-4-(2,2,3-trimethylcyclopent-3-enyl) but-2-en-1-ol, 4-(5,5,6-trimethylbicyclo[2.2.1]hept-2-yl)-cyclohexanol, 2-(2-methyl-propyl)-4-hydroxy-4-methyl-tetrahydropyrane, 2 cyclohexyl propanol, 2-(1,1-dimethyl-ethyl)-4-methyl-cyclohexanol, 1-(2-tert-butyl-cyclo hexyloxy)-2-butanol, 1-(4-isopropyl-cyclohexyl)-ethanol, Limbanol® [1-(2,2,3,6-tetramethyl-cyclohex-1-yl)-3-hexanol, 1 heptanol, 1-nonanol and 10 undecen-1-ol.

2. A perfume formulation according to claim 1, wherein the compound of the formula (I) is capable of assuming a constrained conformation in which the distance between the oxygen of the hydroxy group and the carbon of the esteric function does not exceed 2.8 Ångström for a molecular energy calculated by the method MM2 which differs by no more than 3 kcal/mol from the minimum total energy of the molecule.

3. A perfume formulation according to claim 1, wherein the active ingredient is a compound of formula

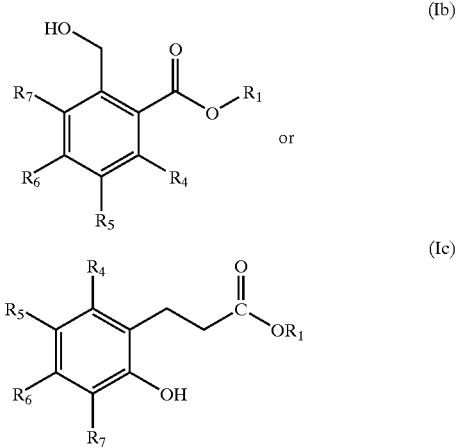

in which the symbols $R_1$, $R_2$ and $R_4$ to $R_7$ are defined as in claim 1.

4. A perfume formulation according to claim 1, wherein the compound of formula (I) is selected from the group consisting of 3-p-menthanyl 2-hydroxymethylbenzoate, 3,7-dimethyl-6-octenyl 2-hydroxymethylbenzoate, 2-phenylethyl 2-hydroxymethylbenzoate, (Z)-3-hexenyl 2-hydroxymethylbenzoate, (E)-3,7-dimethyl-2,6-octadienyl 2-hydroxymethylbenzoate, 1-p-menthen-8-yl 2-hydroxymethylbenzoate, 1,2,2-trimethyl-4-(2',2',3'-trimethyl-3'-cyclopenten-1'-yl)-3-butenyl 2-hydroxymethylbenzoate, (Z)-3-hexenyl dihydrocoumarate and (E)-3,7-dimethyl-2,6-octadienyl dihydrocoumarate.

5. A perfume formulation according to claim 1, in the form of a perfume or an eau de toilette.

6. A perfumed functional article comprising, together with functional constituents of a base, a perfume formulation according to claim 1 or at least one compound of formula (I) as defined in claim 1.

7. A perfumed article according to claim 6, in the form of an after-shave lotion, of a cosmetic preparation, of a soap, a shampoo or conditioner or another hair-care product, of a bath or shower gel, or a foam bath, of a body deodorant or of an air freshener, of a detergent or textile softener, or of an all-purpose product.

8. A method to improve, enhance or modify the odor properties of a composition or product through the release of a perfuming alcohol in the composition or product wherein a compound of formula (I) as defined in claim 1 is added to said composition or product.

9. A process for prolonging the effect of diffusion of the characteristic odor of a fragrant alcohol developed by textiles, characterized in that these textiles are subjected to a washing cycle in the presence of a detergent and, optionally to a subsequent treatment with a textile softener, and the detergent and/or softener contains a compound of formula (I) as defined in claim 1.

10. A compound of formula

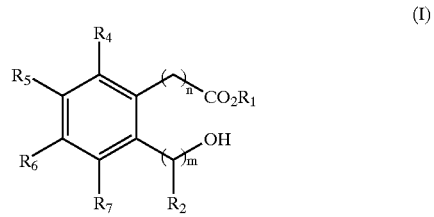

in which $R_1$ represents a radical belonging to a fragrant alcohol of the formula $R_1OH$ selected from the group consisting of anisyl alcohol, fenchyl alcohol, cinnamic alcohol, 9-decen-1-ol, phenethylol, citronellol, 3-methyl-5-phenyl-1-pentanol, 7p-menthan-1-ol, dihydromyrcenol, alpha-ionol, tetrahydro-ionol, nerol, (Z)-3-hexen-1-ol, 1-hexanol, 2-hexanol, 3,3,5-trimethylhexanol, 3,4,5,6,6-pentamethyl-heptan-2-ol, 5-ethyl-2-nonanol, (Z)-6-nonenol, 6,8-dimethyl-2-nonanol, 2,6-nonadien-1-ol, borneol, 1-octen-3-ol, 4-cyclohexyl-2-methyl-2-butanol, 6-ethyl-3-methyl-5-octen-1-ol, 3,7-dimethyl-oct-3,6-dienol, 7-methoxy-3,7-dimethyl-octan-2-ol, methyl-4-phenyl-2-butanol, 2-methyl-1-phenyl-2-propanol, 1-phenylethanol, 2-phenylethanol, 2-phenylpropanol, 3-phenylpropanol, 2-methyl-5-phenylpentanol, 2-methyl-4-phenylpentanol, 3-methyl-5-phenylpentanol, cyclomethyl-citronellol, decanol, dihydroeugenol, 8-p-methanol, 3,7-dimethyl-1-octanol, 2,6-dimethyl-2-heptanol, dodecanol, octanol, undecanol, 4-methyl-3-decen-1-ol, eugenol, tetrahydro-2-isobutyl-4-methyl-4(2H)-pyranol, 2-phenoxy-ethanol, isoeugenol, linalol, 2-methoxy-4-propyl-1-cyclohexanol, vanillin, ethyl-vanillin, anethol, cedrenol, menthol, p-menth-8-en-3-ol, 3,3,5-trimethyl-cyclohexanol, 2,4,6-trimethyl-3-cyclohexenyl-methanol, 4-(1-methylethyl) cyclohexyl-methanol, terpineol, tetrahydromugol, 3,7-dimethyl-3-octanol, (E)-3,3-dimethyl-5-(2',2',3'-trimethyl-3'-cyclopenten-1-yl)-4-penten-2-ol, 2,2,6-trimethyl-alpha-propyl-cyclohexane propanol, 5-(2,2,3-trimethyl-3-cyclopentyl)-3 -methylpentan-2-ol, 3-methyl-5-(2,2,3-trimethylcyclopent-3-enyl)pent-4-en-2-ol, 2-ethyl-4-(2,2,3-trimethylcycloent-3-enyl) but-2-en-1-ol, 4-(5,5,6-trimethylbicyclo[2.2.1]hept-2-yl)-cyclohexanol, 2-(2-methyl-propyl)-4-hydroxy-4-methyl-tetrahydropyrane, 2-cyclohexyl propanol, 2-(1,1-dimethyl-ethyl)-4-methyl-cyclohexanol, 1-(2-tert-butyl-cyclo hexyloxy)-2-butanol, 1-(4-isopropyl-cyclohexyl)-ethanol, 1-(2,2,3,6-tetramethyl-cyclohex-1-yl)-3-hexanol, 1-heptanol, 1-nonanol and 10-undecen-1-ol, m and n define whole numbers within the range 0 to 2 such that the sum m+n is equal to 1 or 2, each of the symbols $R_2$, $R_4$, $R_5$, $R_6$, $R_7$, taken independently, represents a hydrogen atom, a $C_1$ to $C_4$ straight-chain or branched hydrocarbon radical, saturated or unsaturated, optionally substituted.

11. A compound according to claim 10, capable of assuming a constrained conformation in which the distance between the oxygen of the hydroxy group and the carbon of the ester function does not exceed 2.8 Angström for a molecular energy calculated by the method MM2 which differs by no more than 3 kcal/mol from the minimum total energy of the molecule.

12. A compound according to claim 10, wherein the residue of the said compound following release of the perfuming alcohol is odourless.

13. A compound of the formula

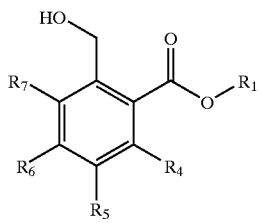

(Ib)

in which R1 represents a radical belonging to a fragrant alcohol of the formula $R_1OH$, comprising at least four carbon atoms, m and n define whole numbers within the range 0 to 2 such that the sum m+n is equal to 1 or 2, each of the symbols $R_4$, $R_5$, $R_6$, $R_7$, taken independently, represents a hydrogen atom, a $C_1$ to $C_4$ straight-chain or branched hydrocarbon radical, saturated or unsaturated, optionally substituted.

14. A compound selected from the group consisting of 3-p-menthanyl 2-hydroxymethylbenzoate, 3,7-dimethyl-6-octenyl 2-hydroxymethylbenzoate, 2-phenylethyl 2-hydroxymethylbenzoate, (Z)-3-hexenyl 2-hydroxymethylbenzoate, (E)-3,7-dimethyl-2,6-octadienyl 2-hydroxymethylbenzoate, 1-p-menthen-8-yl 2-hydroxymethylbenzoate, 1,2,2-trimethyl-4-(2',2',3'-trimethyl-3'-cyclopenten-1'-yl)-3-butenyl 2-hydroxymethylbenzoate, (Z)-3-hexenyl dihydrocoumarate and (E)-3,7-dimethyl-2,6-octadienyl dihydrocoumarate.

15. A product selected from the group consisting of a soap, detergent, cosmetic, perfume, eau de toilette, after shave lotion, shower gel, bath gel, shower soap, bath soap, foam bath, hair care product, such as a shampoo, cosmetic preparation, body deodorant, air-freshener, fabric softener, liquid detergent and solid detergent intended for the treatment of textiles and textile softeners, a detergent for washing dishes or various surfaces, and a cleaning material, the product comprising an active perfuming ingredient according to claim 1.

* * * * *